(12) United States Patent
Lee

(10) Patent No.: US 6,530,873 B1
(45) Date of Patent: Mar. 11, 2003

(54) BRACHYTHERAPY TREATMENT PLANNING METHOD AND APPARATUS

(75) Inventor: Eva K. Lee, Atlanta, GA (US)

(73) Assignee: Georgia Tech Research Corporation

( * ) Notice: Subject to any disclaimer, the term of this patent is extended or adjusted under 35 U.S.C. 154(b) by 0 days.

(21) Appl. No.: 09/697,601

(22) Filed: Oct. 27, 2000

Related U.S. Application Data

(63) Continuation-in-part of application No. 09/375,515, filed on Aug. 17, 1999.
(60) Provisional application No. 60/162,236, filed on Oct. 29, 1999.

(51) Int. Cl.[7] ................................................. A61N 5/00
(52) U.S. Cl. .......................................................... 600/1
(58) Field of Search ............................ 600/1, 2–8, 427, 600/439, 425, 426, 428, 429, 462, 463, 464, 465, 466; 606/108, 130; 128/920–924

(56) References Cited

U.S. PATENT DOCUMENTS 6,095,975 A * 8/2000 Silvern ........................ 600/439
6,327,490 B1 * 12/2001 Spetz .......................... 600/427

* cited by examiner

*Primary Examiner*—Max F. Hindenburg
*Assistant Examiner*—Brian Szmal

(74) *Attorney, Agent, or Firm*—Thomas, Kayden, Horstemeyer & Risley, LLP

(57) ABSTRACT

Techniques for planning the placement of seeds for a brachytherapy treatment of diseased tissue include representing a placement or non-placement of a seed in each point of a predetermined three dimensional grid of potential seed locations with a binary indicator variable. A tumor and surrounding tissue are represented as a predetermined three dimensional tissue grid having a plurality of tissue points. At least one of an upper bound and a lower bound for a dose of radiation received is associated with each point in the tissue grid. An objective value is calculated based on a difference at each point of the tissue grid between an amount of radiation based on a trial placement of seeds and the upper bound or the lower bound of both. The trial placement of seeds is varied and the objective value is again calculated, thereby resulting in additional objective values. An optimal objective value is selected from the calculated objective value and the additional objective values. The planned placement of seeds is set based on the trial placement of seeds that obtains the optimal objective value. Preferably, the tumor and surrounding tissue are represented based on biological imaging. A larger upper bound is preferably associated with fast-proliferating tumor cells than with slowly-proliferating tumor cells. Additionally, the tissue grid may represent the tumor and surrounding tissue at a particular time. In some of these cases, the three dimensional grid of potential seed locations at a time of seed insertion is mapped to a new grid of potential seed locations at the particular time.

40 Claims, 16 Drawing Sheets

BRACHYTHERAPY TREATMENT PLANNING METHOD AND APPARATUS

CLAIM OF PRIORITY

This application claims priority from Provisional Application Serial No. 60/162,236, filed Oct. 29, 1999. This application is a Continuation-in-Part of application Ser. No. 09/375,515, filed Aug. 17, 1999. The entirety of the provisional application and application Ser. No. 09/375,515 are incorporated herein by reference.

BACKGROUND

1. Field of the Inventions

The inventions are related to brachytherapy in general and are specifically related to the placement and dosage of radioactive materials for brachytherapy.

2. Related Art

Brachytherapy is a type of radiation therapy that involves the placement of radioactive sources (referred to herein as "seeds") either in tumors (interstitial implants) or near tumors (intracavity therapy and/or mold therapy). In this treatment approach, radiation from the radioactive sources is emitted outward and is limited to short distances. Thus, unlike external beam radiotherapy, where radiation must traverse normal tissue in order to reach the tumor, brachytherapy is much more localized and therefore reduces radiation exposure to normal tissue while allowing a higher radiation dose as compared to external beam radiotherapy. Brachytherapy has become increasingly popular for the treatment of early-stage prostate carcinoma; therefore, the present inventions will be discussed with reference to the treatment of a prostate tumor. However, those of skill in the art will recognize that the present inventions are not limited to treatment of prostate tumors and that many other uses of the inventions are possible.

In the past, a major limitation to the use of radioactive seed implants was the difficulty of accurately placing the seeds, which may number from approximately 40–100, in a designated geometric pattern. However, with the advent of imaging devices such as transrectal ultrasound (TRUS), it has become possible to image both the prostate and the radioactive seeds. This in turn allows a radiation oncologist greater control in the placement of seeds than had been possible. Seed implantation is commonly performed with a template 300 (a plastic slab with a rectangular grid of holes in it as shown in FIG. 3), which is attached to a TRUS transducer 410 and mounted on a transperineal implantation device 400 as shown in FIG. 4. The TRUS transducer 410 transmits images to a dedicated display unit. A series of transverse images are taken through the prostate, and the TRUS unit displays the template grid superimposed on the prostate image. Needles inserted at the appropriate grid positions enable seed placement in the target at planned locations.

The existence of a suitable procedure for accurately placing seeds raises a second issue: determining the optimal placement (also referred to as the configuration) of the seeds. The placement of seeds should be chosen to satisfy two criteria: a) the sufficiency of the radioactive dose received by the tumor; and b) the minimization of the radioactive dose received by surrounding healthy tissue. The large number of potential configurations means only a small fraction of configurations can be investigated manually.

A number of prior art techniques used to determine seed configurations have been used in the past, including the Manchester Paterson-Parker system, the Quimby system and the Paris system. One problem with these known methods is that they take a large amount of time (on the order of four hours or more) to perform. Thus, treatment strategies devised using these methods are typically generated in a simulation session several days (or weeks) before placement is to be performed. Unfortunately, it is often the case that the position of the diseased organ in the operating room differs from the position of the organ for which the treatment plan was intended. In such cases, it may be necessary to change the plan in the operating room. What is needed is a method and apparatus for quickly (i.e., within minutes) calculating a good brachytherapy treatment plan.

SUMMARY

The aforementioned need is met to a great extent by the present invention which provides an integer linear programming model for the placement of seeds and several techniques for finding optimized solutions for seed placement problems based on the model. The model uses binary (referred to herein as "0/1") indicator variables to represent the placement or non-placement of seeds in a predetermined three-dimensional grid of potential seed locations. In preferred embodiments, the three dimensional grid of potential locations corresponds to the intersections of the rectangular grid of holes of the template discussed above with each of a number of parallel "cuts" of the tumor and surrounding tissue imaged by an imaging device such as a TRUS or CT scanner. The images generated by the imaging device are discretized into a number of image points at a granularity which may or may not be equal to the granularity of the template. The dose delivered to each image point is modeled as a linear combination of the indicator variables. A system of linear constraints is imposed to attempt to keep the dose level at each image point within specified bounds. Branch-and-bound and genetic algorithms are provided to find optimized solutions based on the model. The branch-and-bound and genetic methods may either maximize the sum of rewards associated with achieving the specified bounds or minimize the sum of penalties associated with deviating from the desired bounds.

According to one aspect of the invention, techniques for planning the placement of seeds for a brachytherapy treatment of diseased tissue includes representing a placement or non-placement of a seed in each point of a predetermined three dimensional grid of potential seed locations with a binary indicator variable. A tumor and surrounding tissue are represented as a predetermined three dimensional tissue grid having a plurality of tissue points. At least one of an upper bound and a lower bound for a dose of radiation received is associated with each point in the tissue grid. An objective value is calculated based on a difference at each point of the tissue grid between an amount of radiation based on a trial placement of seeds and the upper bound or the lower bound of both. The trial placement of seeds is varied to obtain an optimal value for the objective value. A planned placement of seeds is set based on the trial placement of seeds that obtains the optimal value for the objective value.

According to one embodiment of this aspect, the tumor and surrounding tissue are represented based on biological imaging. According to another embodiment, a larger upper bound is associated with fast-proliferating tumor cells than with slowly-proliferating tumor cells.

According to another embodiment, the tissue grid represents the tumor and surrounding tissue at a particular time. In some of these embodiments, the three dimensional grid of potential seed locations at a time of seed insertion is mapped to a new grid of potential seed locations at the particular time.

BRIEF DESCRIPTION OF THE DRAWINGS

The foregoing and other features and advantages of the inventions will be more readily understood with reference to the following drawings in which.

DETAILED DESCRIPTION

Figure 1A:
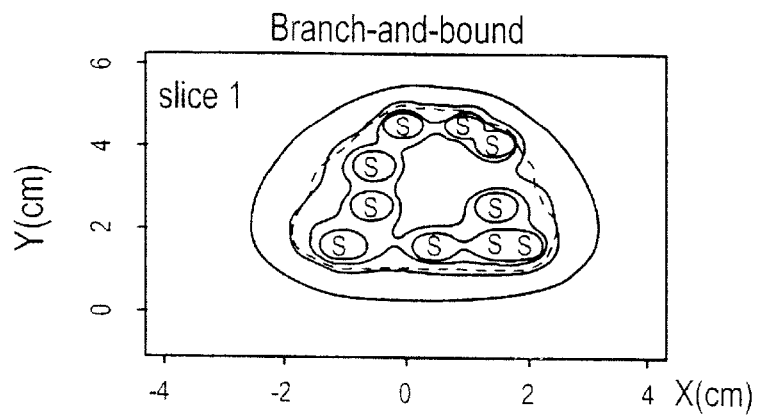
FIGS. 1a and 1n illustrate radiation isodose curves (solid curves) overlaid on prostate contours (dotted curves) for various slices of a patient prostate region for brachytherapy treatment plans obtained with branch-and-bound and genetic methods according to the present inventions.
Figure 1B:
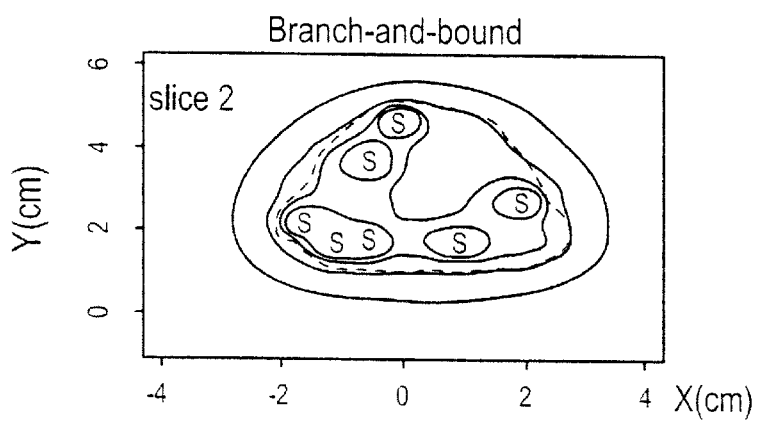
Figure 1C:
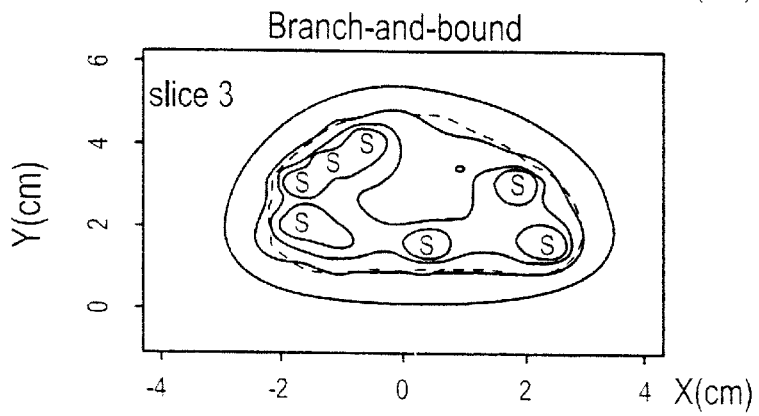
Figure 1D:
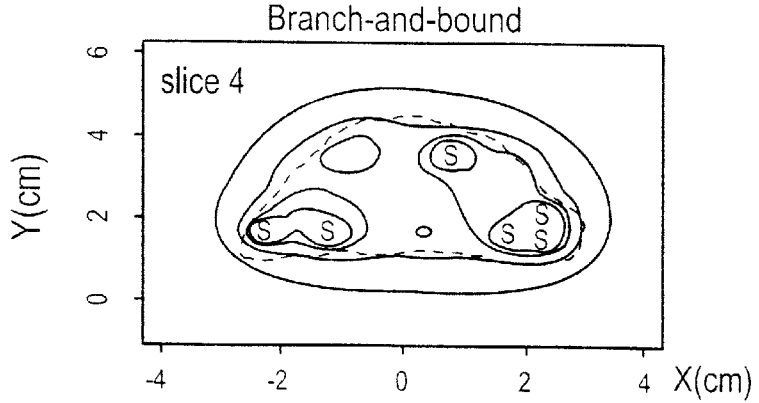
Figure 1E:
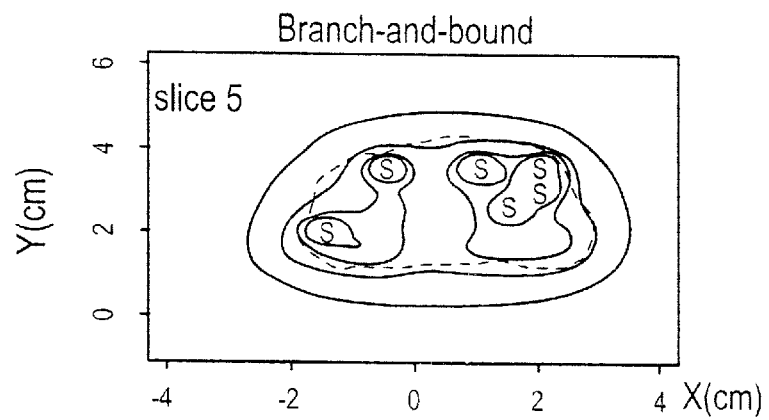
Figure 1F:
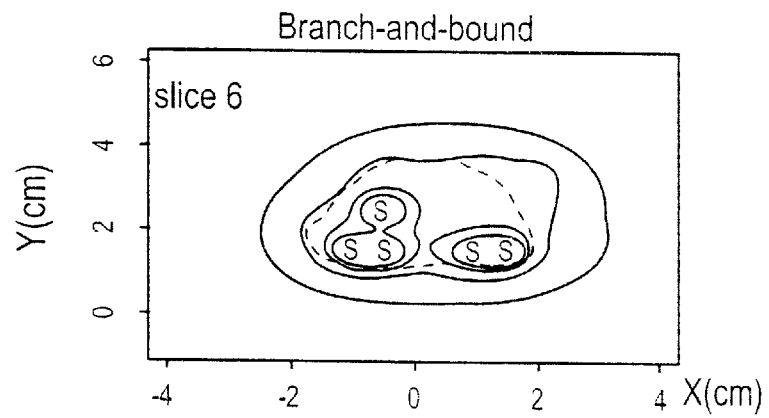
Figure 1G:
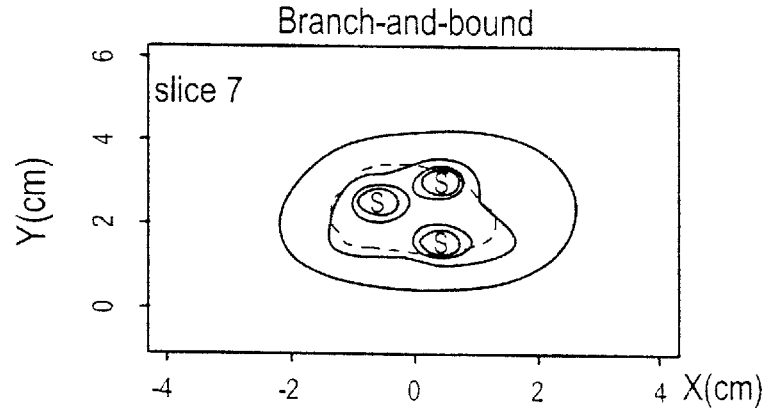
Figure 1H:
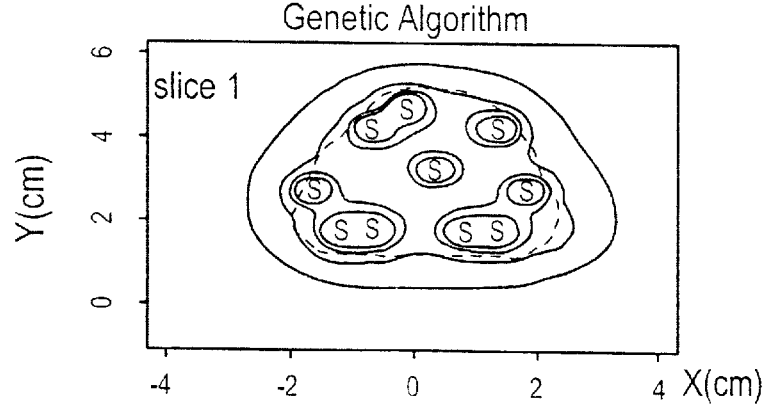
Figure 1I:
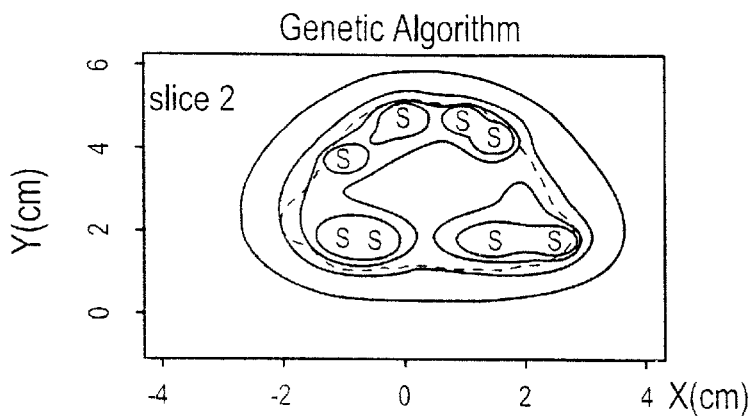
Figure 1J:
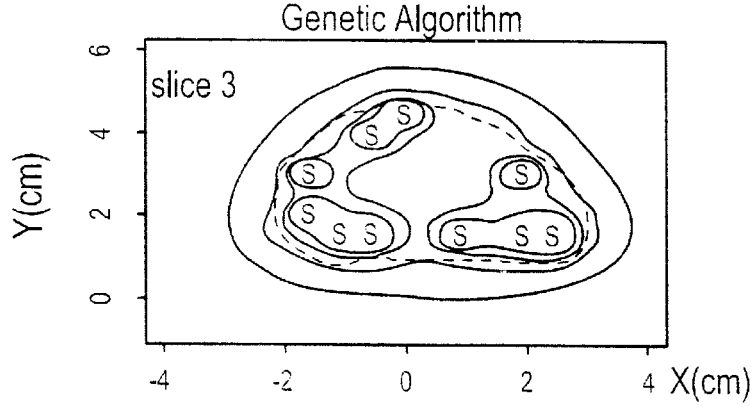
Figure 1K:
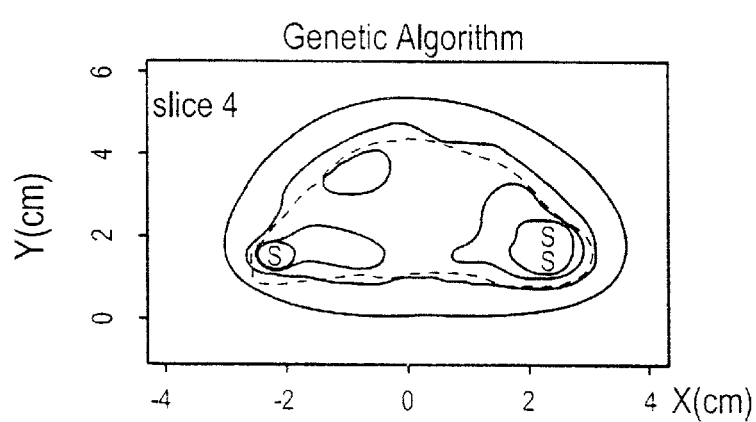
Figure 1L:
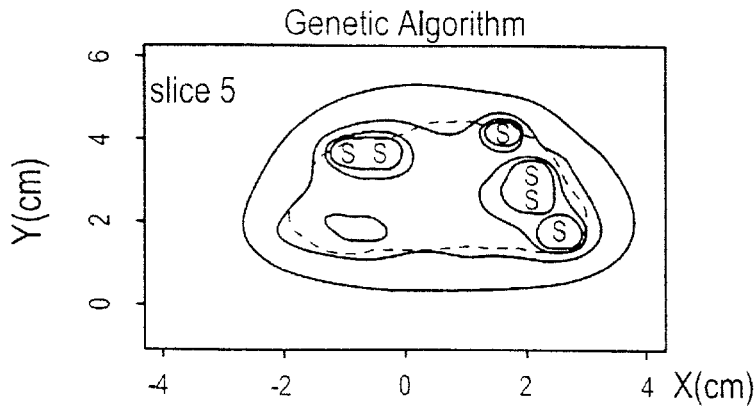
Figure 1M:
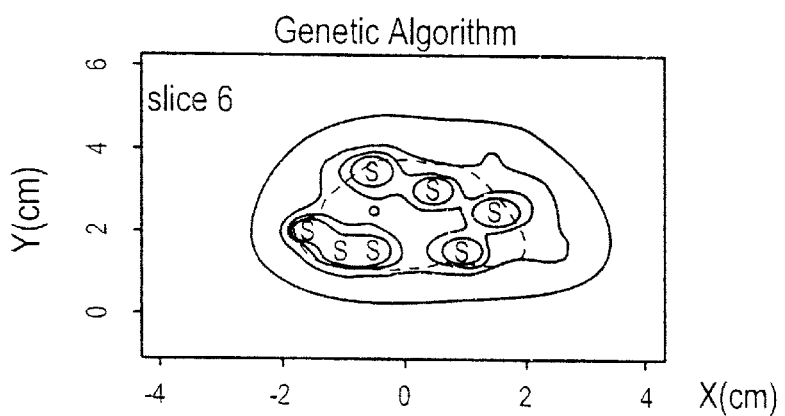

The present inventions will be discussed with reference to preferred embodiments of methods for planning brachytherapy treatments. Specific details, such as the use of a prostate tumor to illustrate the methods, type of imaging device, specific dimensions, numbers of seeds, etc., are set forth in order to provide a thorough understanding of the present inventions. The preferred embodiments discussed herein should not be understood to limit the inventions.

In an ideal situation, it is desirable to develop a treatment plan that provides a sufficient radiation dose (as prescribed by the clinician) to the tumor region while sparing the neighboring healthy tissue from any radiation exposure. However, due to the close proximity of tumor regions and healthy tissue, such a treatment plan does not exist with today's technology. Clinically, in designing treatment plans, one strives to satisfy the prescription dose while providing minimal radiation to healthy, normal tissue. The methods discussed herein involve mixed integer linear programming (MIP) problems. These problems, when solved to proven optimality, will produce optimal treatment plans which satisfy the clinical conditions imposed within the treatment planning models. However, since mixed integer programming problems are NP-hard, as of the date of this application there exists no known algorithm for solving mixed integer programs to proven optimality in "polynomial time." When exact algorithms (e.g., branch and bound) are applied to the MIP treatment planning models and are allowed to run to termination, optimal plans can be obtained. Nevertheless, with the present models, these algorithms can produce near-optimal plans quickly (within 5–15 minutes). Thus, the MIP approach enables clinicians to obtain high-quality treatment plans quickly and therefore handle unforseen situations arising during seed implantation. Therefore, when the terms "optimization" and "optimized" (and variants thereof) are used herein, what is being referred to is "near optimum," as in a near-optimum treatment plan.

Mixed Integer Programming Formulation Basic Model

The mixed integer programming model tissue uses 0/1 variables to record placement or non placement of seeds in a predetermined three-dimensional grid of potential locations. The locations correspond to the intersections of the needles in the template used to place the seeds with each of a number of parallel cuts (imaged by an imaging device such as a TRUS or CT scan device) of the tumor site and neighboring healthy organs. If a seed is placed in a specific location, then it contributes a certain amount of radiation dosage to each point in the images. The images themselves are discretized at a granularity that is conducive both to modeling the problem accurately and to enabling computational approaches to be effective in obtaining solutions in a timely manner. In an application of the method to treat prostate carcinoma, points on the image 2.5 mm apart were selected, resulting in approximately 800–1600 points within the images themselves, plus an additional 300–600 points representing the contours of the images.

The dose contribution of a seed to a point is calculated by assuming each seed is well approximated by a point source. In particular, at a distance r from a seed the dose contribution is given by:

$$D(r) = A\overline{T}\frac{F(r)}{r^2} \tag{1}$$

where A is the initial activity of the seed, $\overline{T}$ is the mean life of the radioisotope, and F(r) is the radial dose factor. In preferred embodiments, an appropriate table of dose factors associated with a discrete set of distances is selected (e.g., see Mohan and Anderson 1982 *Memorial dose distribution computation service—Brachy II interstitial and intracavitary dose computation program user's guide* Memorial Hospital, Appendix I; Anderson et al. 1981, Clinical dosimetry with I-125, *Modern Interstitial and Intracavitary Radiation Cancer Management* George F W (Ed) Masson Publishing USA Inc. 9–15; 1993, A nomograph for permanent implants of Palladium-103 seeds *Int. J. Radiat. Onc. Biol. Phys.* 27 129–135, the contents of which are incorporated by reference herein), and linear interpolation is used to estimate dose factors for distances not in the table. The source emission is actually anisotropic. However, because the source orientation in the patient cannot be controlled, it is assumed that seeds are randomly oriented.

Given the grid of potential seed locations, the total dose level TD at each point P (in Euclidean coordinates) is given by:

$$TD(P) = \sum_{j=1}^{n} D(\|P - X_j\|)x_j, \quad (2)$$

where $x_j$ is a 0/1 indicator variable for recording placement or non placement of a seed in grid position j, $X_j$ is a vector corresponding to the coordinates of grid point j, n is the number of grid points (potential seed locations), and $\|\cdot\|$ denotes the Euclidean norm.

Associated with each point P are target lower and upper bounds, $L_P$ and $U_P$, on the total radiation dose delivered to point P. These bounds are commonly expressed as multiples of a desired prescription dose to the diseased organ, where all points in the same anatomical structure are assigned identical bounds.

Within this framework, the problem of finding a suitable configuration of seeds is interpreted as that of finding a solution to the following system of linear inequalities:

$$\sum_{j=1}^{n} D(\|P - X_j\|)x_j \geq L_P \quad (3)$$

$$\sum_{j=1}^{n} D(\|P - X_j\|)x_j \leq U_P,$$

where each of the variables $x_j$ is restricted to take on either 0 or 1. Unfortunately, it is not possible to satisfy all such inequalities simultaneously as discussed above. Indeed, due to the inverse square factor (see equation (1) above), the dose level contribution of a seed to a point less than 0.3 units away, for example, is typically larger than the target upper bound for the point.

The goal is to devise methods for assigning 0/1 values to the $x_j$'s so that the system is satisfied "to the greatest extent possible" as discussed above. It is natural to consider optimization techniques to achieve this goal. It is necessary to select some metric for gauging "goodness" of solutions before appropriate optimization techniques can be employed. Two general classes of objectives may be used:

(a) maximize the sum of rewards associated with achieving the desired bounds;
(b) minimize the sum of penalties associated with deviating from the desired bounds.

In preferred embodiments, objective (a) is implemented by introducing three nonnegative weights (rewards) for each point. If the dose delivered to point P is greater than or equal to the target lower bound, $L_P$, the objective value is incremented by $\alpha_P \geq 0$; if the dose delivered is less than or equal to the target upper bound, $U_P$, the objective value is incremented by $\beta_P \geq 0$; and finally, if the dose delivered satisfies both bounds, the objective value is incremented by $\gamma_P \geq 0$.

To implement objective (b), two nonnegative weights per point are used in preferred embodiments. If the dose delivered to a point does not satisfy one of the target bounds, a penalty, equal to the deviation from the target bound scaled by the appropriate weight, is added to the objective value. That is, if $TD(P) < L_P$, the objective value is incremented by $\alpha_P[L_P - TD(P)]$, where $\alpha_P \geq 0$. Similarly, if $TD(P) > U_P$, the objective value is incremented by $\beta_P[TD(P) - U_P]$, where $\beta_P \geq 0$. The bounds and weights used in a specific prostate cancer implementation are specified below in Tables 1 and 2.

Incorporating the Objectives

A mixed integer linear program (MIP) is an optimization problem where:

some (possibly all) of the decision variables are restricted to be integer valued,
the decision variables are constrained by a system of linear equations and/or inequalities, and
the objective function to be maximized or minimized is expressed as a linear function of the decision variables.

In order to formulate the basic model outlined above in the mixed integer programming framework, additional variables are introduced to capture the objective goals. For objective (a), one needs to capture when a point satisfies the various bound conditions. Thus, the 0/1 variables $v_P$, $w_P$ and $z_P$ are introduced with the following interpretations:

$$v_P = \begin{cases} 1, & \text{if } TD(P) \geq L_P \\ 0, & \text{otherwise} \end{cases}$$

$$w_P = \begin{cases} 1, & \text{if } TD(P) \leq U_P \\ 0, & \text{otherwise} \end{cases}$$

$$z_P = \begin{cases} 1, & \text{if } L_P \leq TD(P) \leq U_P \\ 0, & \text{otherwise} \end{cases}$$

Then the MIP (mixed integer program) for objective (a) (referred to herein as MIP A) can be stated as:

$$\begin{aligned} &\text{maximize} \sum_{P} (\alpha_P v_P + \beta_P w_P + \gamma_P z_P) \quad \text{(MIP A)}\\ &\text{subject to}\\ &\sum_{j=1}^{n} D(\|P - X_j\|)x_j + N_P(1 - v_P) \geq L_P\\ &\sum_{j=1}^{n} D(\|P - X_j\|)x_j - M_P(1 - w_P) \leq U_P\\ &z_P \leq v_P\\ &z_P \leq w_P\\ &v_P, w_P, z_P, x_j \in \{0, 1\} \end{aligned}$$

where $M_P$ and $N_P$ are suitably chosen positive constants (discussed further below). If a solution is found such that $v_P = 1$, then the term $N_P(1 - v_P)$ in the first inequality in (MIP A) is zero; and hence, the target lower bound for the dose level at point P is satisfied. Similarly, if $w_P = 1$, the term $M_P(1 - w_P)$ in the second inequality in (MIP A) is zero; and hence, the target upper bound for the dose level at point P is satisfied. Finally, if $z_P = 1$, then both $v_P = 1$ and $w_P = 1$, and consequently, the dose level delivered to point P satisfies both bounds. The objective, maximize $\Sigma_P(\alpha_P v_P + \beta_P w_P + \gamma_P z_P)$, is what drives the optimization engine to assign a value of 1 to the variables $v_P$, $w_P$ and $z_P$. In particular, at optimality, the converse of each of the above conditional statements is true, provided the associated objective coefficient is strictly positive. Formally, if $\alpha_P > 0$, then at optimality, $v_P = 1$ if and only if the target lower bound at point P is satisfied;
if $\beta_P > 0$, then at optimality, $w_P = 1$ if and only if the target upper bound at point P is satisfied; and
if $\gamma_P > 0$, then at optimality, $z_P = 1$ if and only if the dose delivered to point P satisfies both bounds.

The argument to establish the "if" direction in each of the above statements is elementary. For example, consider the first statement. If the target lower bound at point P is satisfied, but $v_P = 0$, then the current solution is not optimal since a better solution can be found by modifying the current solution. The modified solution is selected identical to the current solution except the variable $v_P$ is assigned the value 1 instead of 0. Thus, the modified solution has an objective value that exceeds the current (supposedly optimal) solution by $\alpha_P$.

The role of the constants $N_P$ and $M_P$ in (MIP A) is to ensure that there will be feasible solutions to the mathematical model. In theory, these constants should be chosen large enough so that if $v_P$ or $w_P$ is zero, the associated constraint in (MIP A) will be satisfied regardless of how the 0/1 variables $x_j$ are assigned. In practice, the choice is driven by computational considerations of the optimization algorithm being used and/or by decisions by the radiation oncologist. For the genetic algorithm described below, these constants are irrelevant since the algorithm does not depend on the constraints at all. For the branch-and-bound algorithm described below, the constants are needed, and it is advantageous computationally to assign values that are as small as possible. The radiation oncologist can guide the selection of the constants by either declaring absolute extremes on acceptable radiation dose levels delivered to each point (note that $U_P+M_P$ is the absolute maximum dose level that will be delivered to point P under the constraints of (MIP A), and $L_P-N_P$ is the absolute minimum), or by estimating the number of seeds needed for a given plan. In the latter case, if the number of seeds needed is estimated to be between 80 and 120, for example, then the constant $N_P$ can be taken to be $L_P$ minus the sum of the smallest 80 of the values $D(\|P-X_j\|)$, and the constant $M_P$ can be taken to be the sum of the largest 120 such values minus $U_P$. Selection in this fashion will ensure that no plan having between 80 and 120 seeds will be eliminated from consideration.

For objective (b), nonnegative continuous variables $\gamma_P$ and $z_P$ are introduced to capture the deviations of the dose level at a given point from its target lower and upper bounds, respectively. The MIP for objective (b) (MIP B) can be stated as:

maximize $\Sigma_P(\alpha_P\gamma_P+\beta_P z_P)$ subject to $$\text{subject to} \sum_{j=1}^{n} D(\|P - X_j\|)x_j + \gamma_P \geq L_P \quad \text{(MIP B)}$$

$$\sum_{j=1}^{n} D(\|P - X_j\|)x_j - z_P \leq L_P$$

$$\gamma_P \geq 0, z_P \geq 0, x_j \in \{0, 1\}.$$

When applied to (MIP B), an optimization engine will attempt to assign values to the 0/1 variables (i.e., select seed positions from the set of potential seed positions) so that the weighted sum of deviations from the target bounds, $\Sigma_P(\alpha_P\gamma_P+\beta_P w_P)$, is minimized. Note that it is the objective that drives the optimization engine to select $\epsilon_P$ and $z_P$ to represent the deviations. Indeed, at optimality, any constraint for which $\gamma_P(z_P)$ is non zero will be satisfied at equality, provided that $\alpha_P(\beta_P)$ is strictly positive.

In both models, the objective function weights ($\alpha_P$, $\beta_P$, $\gamma_P$) should be selected according to the relative importance of satisfying the associated bounds. For example, weights associated with an upper bound on the radiation dose for points in a neighboring healthy organ may be given a relatively larger magnitude than weights associated with an upper bound on the dose level for points in the diseased organ. In a similar spirit, the lower and upper bounds, $L_P$ and $U_P$, can be selected to guide the optimization engine to select solutions with desired characteristics. Given a target prescription dose for the diseased structure, the dose delivered to points on the boundary of the structure could be tightly controlled by appropriately selecting lower and upper bounds (e.g., 100% and 115% of the prescription dose) for points representing the contours of the structure, while other points within the diseased structure could be restricted by a much wider range of bounds (e.g., 100% and 160% of the prescription dose). In this way, the dose to tissue outside of the diseased structure is effectively controlled. The selection of a set of weights and bounds may be guided by analysis of solutions via other criteria, such as isodose curves and dose-volume histograms. Such criteria helped to influence the choice of weights and bounds for application of the models to the prostate cancer cases discussed herein.

Model Variations

Various simplifications to (MIP A) are possible depending on how the objective coefficients and bounds are selected. For example, if it is desired to add a reward only if both target bounds at point P are satisfied, then one would select $\alpha_P=0$, $\beta_P=0$ and $\gamma_P>0$. In this case, the variables $\alpha_P$ and $w_P$ can be replaced with $z_P$ and the constraints $z_P \leq v_P$ and $z_P \leq w_P$ can be eliminated. Another opportunity for simplification may arise if P represents a point in healthy tissue. In this case it may be reasonable to assign $L_P=0$; then the variable ˜$_P$ and the constraints involving $\alpha_P$ can be eliminated.

When the target bounds $L_P$ and $U_P$ are expressed as multiples of a target prescription dose, $T_P$, another natural approach is to capture the deviations from $T_P$ directly. In our model, this can be achieved by replacing constraints (3) with:

$$\sum_{j} D(\|P - X_j\|)x_j + \gamma_P = T_P \quad (4)$$

where $\gamma_P$ is a continuous variable, unrestricted in sign. In the objective, one can then minimize the q norm of the vector $\gamma$ of all deviations; i.e., minimize $\|\gamma\|_q=(\Sigma_P|\gamma_P|^q)^{1/q}$.

Another enhancement that could be incorporated into any of the above models is the allowance of alternative seed types, or possibly same seed types but having different source activities. There are a variety of radioactive sources that are used for brachytherapy, including cesium-137, iridium-192, palladium-103, iodine-125, and gold-198, each of which has its own set of exposure rate constants. Typically, however, a single seed type is used in a given treatment plan. This fact is, in part, due to the difficulty of designing treatment plans with multiple seed types. The allowance of multiple seed types can easily be incorporated into the MIP model—one need only modify the total dose level expression (2) as:

$$\sum_{j}\sum_{i} D_i(\|P - X_j\|)x_{ij} \quad (5)$$

Here, $x_{ij}$ is the indicator variable for placement or non placement of a seed of type i in grid location j, and $D_i(r)$ denotes the dose level contribution of a seed of type i to a point r units away. In this case, a constraint restricting the number of seeds implanted at grid point j is also needed: $\Sigma_i x_{ij} \leq 1$. It remains to be tested whether the added flexibility of allowing multiple seed types will have a substantial impact on the number of points at which the target dose levels can be satisfied. Computationally, the optimization problem may prove to be more difficult due to the increased number of 0/1 variables.

Finally, the basic model also allows the incorporation of additional physical constraints. For example, one could incorporate constraints to control the percentage of each tissue structure satisfying the specified bounds.

Alternatively, one could, if desired, constrain the total number of seeds and/or needles used.

Computational Techniques

Two computational methods have been applied to instances of the models presented in the previous section to find an optimized solution. The first method, known as branch-and-bound, is an exact method commonly employed in solving integer programming problems. A branch-and-bound algorithm will, if allowed to run to completion, terminate with an optimal solution. Moreover, the "intelligent" search mechanism of the branch-and-bound method enables large sections of the solution space to be eliminated from consideration (knowing that no solution within can be optimal) without actually examining each solution within—thereby conserving computing time.

The second approach is a genetic algorithm. A genetic algorithm is a heuristic procedure, and is applied in this case without taking into account any constraints in the model. It is based on the idea of randomized enumeration, where the randomization is guided by operations designed to mimic the phenomena of crossover and mutation that naturally occur in the reproduction of species. The notion that only the best fit individuals survive to pass on their genetic material is mimicked by biasing the selection of parents by using a "fitness" function based on the objective function that is to be optimized. Although genetic algorithms have been applied with some success to combinatorial optimization problems, they are only heuristic search strategies. No test for optimality is embedded into a genetic algorithm. The user of the algorithm dictates that the algorithm should terminate either after a specified number of generations, or after the observed change in fitness scores between consecutive generations remains sufficiently small.

Branch-and-Bound Method

The classical approach to solving linear 0/1 mixed integer programs is branch-and-bound. This is a tree search approach where, at each node of the tree, certain binary variables are fixed to zero or one, and the remaining binary variables are relaxed (i.e., allowed to assume any value between zero and one). This results in a linear program (LP) being associated with each node of the tree. The LP at the root node is simply the original 0/1 MIP instance with all of the binary variables relaxed. The tree is constructed such that the binary is variables fixed in a parent node will be fixed identically in any of its children, and each child will have an additional binary variable fixed to zero or one. Typically, children are formed in pairs as follows. Assume that the LP at a given node is solved, and one or more of the relaxed binary variables is fractional in the optimal solution. One selects such a fractional binary variable and branches on it. That is, two child nodes are formed; one with the selected binary variable fixed to zero, and the other with the selected binary variable fixed to one. Of course, each child also inherits all of the fixed binary variables of its parent. Note that the objective value of a child node can be no greater (in the case of maximization) than the objective value of its parent.

If the linear program at a given node is solved and the optimal solution happens to have integral values for all the relaxed binary variables, then this solution is feasible for the original 0/1 mixed integer program. Once a feasible solution for the original problem is found, the associated objective value can be used as a lower bound (in the case of maximization) for the objective values of LP's at other nodes. In particular, if an LP at another node is solved, and its objective value is less than or equal to the lower bound, then none of its children could yield a feasible solution for the original MIP with a greater objective value than the one already obtained. Hence, no further exploration of this other node is needed, and the node is said to be fathomed.

Two other criteria for fathoming a node are obvious: if the associated LP is infeasible, or if the optimal solution of the LP has integral values for all relaxed binary variables, then no further exploration of the node is required. In the latter case, the optimal objective value of the LP will be compared with the current lower bound, and the lower bound will be updated if needed. The tree search ends when all nodes are fathomed.

A variety of strategies have been proposed for intelligently selecting branching variables and nodes to process. However, no strategy stands out as being best in all cases. What has become clear from recent research in computational MIP, is that branch-and-bound is most effective when coupled with other computational devices, such as problem preprocessing, primal heuristics, global and local reduced-cost fixing, and cutting planes. The reader can refer to the article by Lee and Mitchell (1999, Branch-and-bound methods for integer programming *Encyclopedia of Optimization* Floudas C A and Pardalos P M (Eds.) (The Netherlands: Kluwer Academic Publishers), the contents of which are incorporated by reference herein), for a concise description of branch-and-bound methods for integer programming. The books by Schrijver (1986, *Linear and Integer Programming* (New York: Wiley)), Nemhauser and Wolsey (1988, *Integer and Combinatorial Optimization* (New York: Wiley)) and Parker and Rardin (1988, *Discrete Optimization* (New York: Academic Press), the contents of which are incorporated by reference herein), contain detailed expositions on integer programming and related computational issues.

The numerical work of the preferred embodiments discussed herein is based on a branch-and-bound MIP solver that is built on top of a general-purpose mixed integer research code (MIPSOL) (Lee 1997, Computational experience of a general purpose mixed 0/1 integer programming solver, Technical Report School of Industrial and Systems Engineering Georgia Institute of Technology, the contents of which are incorporated by reference herein). The general-purpose code, which incorporates all of the above mentioned computational devices, has been shown to be effective in solving a wide variety of large-scale real-world MIP instances. A complete description of the solver and comparisons between numerical strategies are described in Lee et al. (1998a, Computational issues for a mixed integer programming approach to treatment plan optimization for radiation therapy, Technical Report School of Industrial and Systems Engineering Georgia Institute of Technology; 1998b, Mixed integer programming approaches to treatment planning for brachytherapy—application to permanent prostate implants, Technical Report School of Industrial and Systems Engineering Georgia Institute of Technology, the contents of which are incorporated by reference herein).

Genetic Method

A genetic algorithm is a heuristic optimization method modeled on the biological mechanisms of evolution and natural selection (e.g., see Buckles 1992, *Genetic Algorithms* (Los Alamitos, Calif.: IEEE Computer Society Press); Wasserman 1993, *Advanced Methods in Neural Computing* (New York: Van Nostrand Reinhold, the contents of which are all incorporated by reference herein). In nature, the characteristics of an organism are encoded in streams of DNA known as chromosomes. Likewise, in a genetic algorithm, a potential solution to a problem is encoded as a stream of symbols over a given alphabet. Given an initial population of individuals (i.e., potential solutions encoded as symbol streams), a subset of the population is selected to parent offspring for the next generation. The parent selection process is stochastic, but biased towards selecting those individuals that are most fit, as measured by a pre-selected fitness function (e.g., the objective function that one is trying to optimize).

After the parents are selected, they are paired off and mated. That is, subsections of two parent symbol streams are interchanged, forming two new members for the next generation. This is analogous to cross-over in biological reproduction, where a child's genetic composition is a combination of its parents. Mutations are also possible. This is typically implemented by randomly selecting a child symbol stream and randomly altering one of its symbols.

The algorithm can be terminated after a specified number of generations have been created (usually several hundred), or by examining when the difference between the maximum and minimum fitness values between consecutive generations remains less than a specified threshold for a number of generations. Upon termination, the individual in the final generation with the largest fitness value is selected as the operative solution to the problem at hand.

Obviously, many variations on implementation specifics for a genetic algorithm are possible. For the case at hand, a given seed configuration can be viewed as a stream of 0's and 1's. In terms of the notation in the previous section, such a stream is analogous to an instantiation of the binary variables $x_j$.

The genetic algorithm described herein begins by randomly generating 600 binary data streams of length n, all having the same number of 1's (an initial estimate of the number of seeds required). From this set of 600, the top scoring 15, excluding duplicates, are selected for the first generation. Subsequent generations all have 15 members as well. To create the next generation from the current generation, 14 of the 15 data streams are selected to be involved in a crossover and paired up. For the crossover operation, non-contiguous randomly selected bits are interchanged. A uniformly distributed random number between 0 and n/2 is used to determine the number of bits to be interchanged between parent pairs.

After cross-over occurs, the mutation operation is performed five times. Each operation involves randomly selecting one of the 15 data streams (14 newly created data streams resulting from crossover, plus the one data stream that was not selected to be a parent) and randomly selecting a bit to be inverted. Note that the same data stream could be selected two or more times for mutation, and, though unlikely, one mutation could cancel the effect of a previous mutation.

In order to ensure that the current best solution is not lost, the strategy of elitism is employed. That is, the data stream with the highest fitness value is passed on unchanged to the next generation. This is implemented by simply overwriting one of the newly created children. More details on the implementation of the genetic algorithm can be found in Silvern (1998, Automated OR prostate brachytherapy treatment planning using genetic optimization, Ph.D. Thesis, Department of Applied Physics, Columbia University, New York, the contents of which are incorporated by reference herein).

Numerical Experiments

Data from 20 prostate cancer patients were used to test the models and algorithmic approaches discussed above. The data included points representing the discretization of three anatomical structures—the prostate, the rectum, and the urethra. Two distinct categories of points were used to represent the prostate. Contour points specified the boundary of the prostate in each of the images; and the regions determined by each boundary were populated with uniformly spaced points, referred to herein as uniformity points. Within each image, both the contour points and the uniformity points were spaced 2.5 mm apart in each dimension. The images themselves were spaced 5 mm apart. In addition to the discretization data, isotope source activities and radial dose factors, and coordinates of potential seed locations were also specified.

The results described herein facilitate two objectives: (1) to assess the effects of using the different models and model parameters, and (2) to compare plans obtained by the branch-and-bound optimization approach to those obtained by the genetic algorithm approach. To facilitate objective (1), a single optimization algorithm (the branch-and-bound algorithm) was applied to each model and the objective weights were varied in an identical manner across models. Comparison between treatment plans was based on quantitative measures of the percentage of points in each anatomical structure achieving specified target dose bounds, as well as by visual inspection of dose-volume histograms and isodose curves. To facilitate objective (2), a single model and objective weight combination was selected for each method, and each method was applied to all 20 patient cases. Comparison between treatment plans obtained with the two methods was performed using the same criteria as in goal (1).

Choice of Model Parameters

The models described above offer many degrees of freedom for assigning target bounds and objective function weights. For example, each point in the discretization can be assigned its own unique set of bounds and weights. In preferred embodiments, however, it is reasonable to stratify the assignment of bounds and weights by point type. Thus, for each point type (i.e., contour, uniformity, rectum, and urethra), a target lower bound, a target upper bound, and three objective function weights were assigned.

The target bounds used are shown in Table 1. They are expressed as multiples of the

TABLE 1

|   | Rectum | Urethra | Uniform | Contour |
|---|--------|---------|---------|---------|
| L | 0.00   | 1.00    | 1.00    | 1.00    |
| U | 0.78   | 1.50    | 1.60    | 1.60    | target prescription dose to the prostate, which was patient dependent. Note that the lower bound for rectum points was set to zero, since there is no therapeutic reason to deliver any radiation to the rectum. In contrast, since the urethra is surrounded by the prostate, too little dosage to the urethra may be indicative that diseased tissue proximal to the urethra is not receiving adequate dosage. Hence, a positive-valued lower bound for urethra points was specified. One may argue that there is no therapeutic reason to place upper bounds on the dose delivered to points representing the prostate. However, from the optimization standpoint, there is an important reason. If no upper bounds are specified, the optimization engine will be guided by an objective that emphasizes the satisfaction of lower bounds, and thus will steer towards solutions that have an over abundance of seeds. The upper bounds on uniformity and contour points effectively help to limit the number of seeds selected, and thereby confine the prescription dose to the diseased tissue.

Extensive computational experiments were performed to study the effects of using different objective function weights for the various point types. Initial observations revealed that it was advantageous to assign weights based, at least in part, on the number of points in the discretization of each "structure." Here, we summarize results for the weight combinations given in Table 2. The symbols $n_r$, $n_{ur}$, $n_{un}$, and $n_c$: denote, respectively, the

TABLE 2

| Combination | Parameter | Rectum | Urethra | Uniform | Contour |
|---|---|---|---|---|---|
| 1 | α | 0 | $n_{un}/n_{ur}$ | 1 | $n_{un}/n_c$ |
|  | β | $n_{un}/n_r$ | $n_{un}/n_{ur}$ | 1 | $n_{un}/n_c$ |
|  | γ | 0 | 0 | 0 | 0 |
| 2 | α | 0 | $n_{un}$ | 1 | 1 |
|  | β | $n_{un}$ | $n_{un}$ | 1 | 1 |
|  | γ | 0 | 0 | 0 | 0 |
| 3 | α | 0 | 0 | 0 | 0 |
|  | β | 0 | 0 | 0 | 0 |
|  | γ | $n_{un}/n_r$ | $n_{un}/n_{ur}$ | 1 | $n_{un}/n_c$ |
| 4 | α | 0 | 0 | 0 | 0 |
|  | β | 0 | 0 | 0 | 0 |
|  | γ | $n_{un}$ | $n_{un}$ | 1 | 1 | number of rectal points, the number of urethra points, the number of uniformity points, and the number of contour points. For the 20 cases considered, $n_{un}$ ranged between 568 and 2206, $n_c$ between 261 and 692, and $n_r$ and $n_{ur}$ between 6 and 10. (In each image, the positions of the rectum and urethra were each represented by a single point.)

Combinations 1 and 3 correspond to giving equal weight to each structure by taking into account how many points represent each structure. The uniformity points are the most numerous, so each uniformity point is weighted by 1, and each non uniformity point is weighted by the number of uniformity points divided by the number of points representing the associated structure. In combinations 2 and 4, each point representing the prostate is weighted by 1, and the rectum and urethra points are weighted by the number of uniformity points. The use of the large weights on rectum and urethra points in Combinations 2 and 4 greatly increases the likelihood that the optimization engine will select a solution for which the dose delivered to these points will be within the target bounds.

Including both combinations 1 and 2 (and similarly, 3 and 4) the numerical tests provided a way of gauging the sensitivity of treatment plans obtained to relatively small changes in contour point priority. The motivation for weighting contour points higher is to drive the optimization engine to select a solution in which the target prescription dose conforms well to the prostate, thereby reducing excessive exposure to nearby healthy tissue. In the 20 cases considered, the ratios $n_{un}/n_c$ ranged between 1.98 and 3.41, so the shift in priority is relatively small. Finally, the relative importance of allocating rewards (penalties) for satisfying (violating) bounds separately versus satisfying both bounds simultaneously can be analyzed by comparing results of using weight combinations 1 and 3, as well as weight combinations 2 and 4.

Note that all four weight combinations are directly applicable to (MIP A), whereas only combinations 1 and 2 are directly applicable to (MIP B). However, combinations 3 and 4 could be applied to a modified form of (MIP B) involving additional constraints and variables. Also note that since the lower bound for rectal points is set to zero (see Table 1), these points always achieve the lower bound; and consequently, there is no need to allocate a positive reward to the α parameter for the rectum in combinations 1 and 2.

Numerical Results

All treatment plans discussed herein were generated on 166 Mhz machines. Plans from the branch-and-bound algorithm were those associated with the first feasible solutions found (i.e., integer-valued, but not necessarily optimal), and were obtained within 300 CPU seconds. For the genetic algorithm, typically 1000 generations were used for generating a treatment plan, requiring approximately 900 CPU seconds.

For the evaluation of treatment plans, a much finer grid (1 mm spacing in each dimension) of uniformity points was used. This not only helped to obtain a more complete representation of dose delivered to the prostate, it also helped to eliminate the bias of testing a plan with the same data used to generate it. Plans were also evaluated using a smaller upper bound on the contour points than used in the models themselves. Visual inspection of isodose curves and dose-volume histograms showed that plans for which a significant number of contour points were within 115% of the prescription dose conformed quite well to the prostate volume. Hence, although the models upon which the plans were generated used an upper bound of 1.6 times the prescription dose, a factor of 1.15 was used in the evaluation phase.

In both (MIP A) and (MIP B), the initial plans obtained using weight combination 2 satisfied more bound conditions for urethra and rectum points than those obtained using weight combination 1. In (MIP A2) (i.e., (MIP A) with weight combination 2) 100% of the urethra and rectum points satisfied both bounds in 17 cases, while in the remaining 3 cases, approximately 80% of the points satisfied both bounds. In contrast, for (MIP A1) only 8 cases achieved 100% satisfaction of both bounds. In the remaining 12 cases, the percentage of points satisfying the upper bound ranged from 50–100%, and the percentage of urethra points satisfying the lower bound ranged from 80–100%. (Again, rectal points automatically satisfy their specified lower bound of zero.) For (MIP B2), in all 20 cases, all urethra points satisfied the lower bound and over 85% of rectum and urethra points satisfied the upper bound. For (MIP B1), in 19 cases, all urethra points satisfied the lower bound, and in all 20 cases, between 40–85% of urethra and rectum points satisfied the upper bound. There are two factors contributing to the observed results. First, and likely more important, the urethra and rectum points are weighted significantly heavier in combination 2 than in combination 1. Second, the contour points are weighted somewhat less in combination 2 than in combination 1. Thus, for (MIP A2) and (MIP B2) the optimization engine will tend to select solutions in which the urethra and rectum points satisfy their bounds, and at the same time give relatively less emphasis (compared with (MIP A1) and (MIP B1)) to contour point bounds.

By the same token, one would expect more contour points to satisfy the measured bounds when using weight combination 1 than when using weight combination 2. We observed this to a small degree for (MIP A), but since the ratios $n_{un}/n_c$ were typically 3 or less, there was not a great difference. Among the 20 cases, for (MIP A1) on average 31% of contour points satisfied both bounds, 53% satisfied the upper bound, and 79% satisfied the lower bound. The corresponding percentages for (MIP A2) were 28%, 51%, and 77%. In 16 cases, there were at least as many contour points satisfying both bounds for (MIP A1) as there were for (MIP A2). The increase in the percentage of points satisfying both bounds ranged from 0% (5 cases) to 12%. In the four remaining cases, there were modestly more contour points (less than 2%) satisfying both bounds in (MIP A2) than in (MIP A1). In 14 cases, the percentage of contour points with dose level less than the upper bound was higher (by 0%–13%) in (MIP A1) than in (MIP A2), while in 6 cases it was lower (by 0%–4%). Perhaps more significant, the percentage of contour points at a dose level greater than 250% of the prescription dose was lower (by 0.3%–2.5%) in every patient case in (MIP A1) compared to (MIP A2). These results provide evidence to support the hypothesis that (MIP A) allows fairly fine-grain control of dose to contour points via incremental changes in weights associated with satisfying contour point bounds.

The results regarding contour points for (MIP B) under weight combinations 1 and 2 were mixed. In particular, weight combination 1 did not, in general, lead to the satisfaction of more bound conditions on contour points than did weight combination 2. This, together with the discussion in the previous paragraph, suggests that results of small weight adjustments to (MIP B) are less predictable than those to (MIP A).

The primary issue for uniformity points concerns the satisfaction of the lower bound so as to ensure the prostate receives a full tumoricidal dose. For all models and weight combinations, on average 96%–97% of uniformity points achieved a dose level greater than or equal to the prescription dose. Of particular interest, however, is that there was one patient case (Patient 17) in which all models scored well below average (83%–87%). This anomaly occurred for the genetic algorithm as well as the branch-and-bound algorithm (see Table 3. and FIG. 2). Visual inspection of the contours for this case showed that they tapered off unusually sharply at both ends. The fact that all models and weight combinations returned similar results for this case suggests that this distinguishing physical feature of the prostate makes it significantly more difficult to find a plan with "desired" characteristics.

When the branch-and-bound algorithm was applied to (MIP A) using weight combinations 3 and 4, among the 20 patient cases, on average only 50% of the uniformity points satisfied the lower bounds, and less than 10% of the contour points were within both bounds (approximately 8% satisfied the lower bound, while over 90% satisfied the upper bound). These results suggest that initial solutions obtained from the branch-and-bound algorithm for these latter weight combinations yield plans that are inferior to those obtained via weight combinations 1 and 2. Overall, for the 20 cases considered, the best treatment plans generated from the branch-and-bound algorithm resulted from its application to (MIP A1).

In contrast, empirical tests using the genetic algorithm showed that, among the weight combinations used to test it, it yielded the best plans when applied to (MIP A) and a variant of weight combination 3 in which the y parameters were set to 35, 40, 1, and 3 for the rectum, urethra, uniformity, and contour points, respectively (Silvern 1998, Automated OR prostate brachytherapy treatment planning using genetic optimization, Ph.D. Thesis, Department of Applied Physics, Columbia University, New York). Table 3 shows a comparison of plans from the branch-and-bound algorithm applied to (MIP A1) and the genetic algorithm applied to (MIP A) using the above weights. Patient cases are categorized according to the prescription dose. The source activity of seeds used is specified in the column labeled Activity. For each algorithm, the first three columns—labeled $\geq 100\%$, $\leq 115\%$, $\geq 250\%$—correspond to the percentage of contour points satisfying at least 100%, at most 115%, and above 250% of the prescription dose, respectively. Next, the column $\geq 100\%$ indicates the percentage of uniformity points satisfying at least 100% of the prescription dose. Finally, No. Seeds denotes the number of seeds used in the generated plans.

TABLE 3

| | | Branch-and-Bound | | | | | Genetic Algorithm | | | | |
|---|---|---|---|---|---|---|---|---|---|---|---|
| | | Contour | | | Uniformity | | Contour | | | Uniformity | |
| | Activity | Percent of Points Achieving | | | | | Percent of Points Achieving | | | | |
| Pat. | (mCi) | $\geq 100\%$ | $\leq 115\%$ | $\leq 250\%$ | $\geq 100\%$ | No. Seeds | $\geq 100\%$ | $\leq 115\%$ | $\leq 250\%$ | $\geq 100\%$ | No. Seeds |
| | | | | 100 Gy | | | | | | | |
| 1 | 0.592 | 77.5 | 50.8 | 2.02 | 97.3 | 40 | 76.5 | 54.4 | 3.70 | 96.1 | 40 |
| 2 | 0.450 | 85.2 | 60.8 | 0.96 | 99.4 | 51 | 94.8 | 41.3 | 3.85 | 99.6 | 54 |
| 3 | 0.334 | 73.2 | 50.9 | 3.26 | 94.5 | 51 | 71.6 | 57.6 | 3.26 | 93.2 | 50 |
| 4 | 0.400 | 87.3 | 55.0 | 2.16 | 98.5 | 42 | 83.2 | 46.7 | 6.47 | 97.5 | 42 |
| 5 | 0.590 | 80.5 | 52.8 | 1.08 | 98.5 | 50 | 84.8 | 46.1 | 2.48 | 97.1 | 51 |
| 6 | 0.450 | 86.4 | 48.3 | 2.69 | 98.6 | 64 | 87.5 | 43.6 | 7.47 | 98.7 | 62 |
| 7 | 0.400 | 90.1 | 43.5 | 4.80 | 97.0 | 39 | 84.8 | 43.9 | 7.58 | 96.1 | 38 |
| 8 | 0.450 | 80.0 | 55.2 | 1.85 | 98.3 | 44 | 93.0 | 37.6 | 4.85 | 99.4 | 46 |
| 9 | 0.500 | 90.0 | 43.4 | 2.22 | 98.8 | 32 | 90.8 | 39.7 | 6.39 | 98.0 | 32 |
| | | | | 120 Gy | | | | | | | |
| 10 | 0.468 | 81.3 | 42.6 | 1.15 | 93.9 | 28 | 72.8 | 59.0 | 4.60 | 92.7 | 28 |
| | | | | 160 Gy | | | | | | | |
| 11 | 0.520 | 75.5 | 58.0 | 0.87 | 96.4 | 85 | 72.4 | 52.9 | 3.47 | 94.2 | 82 |
| 12 | 0.544 | 75.6 | 48.8 | 2.85 | 95.1 | 58 | 73.9 | 48.7 | 5.69 | 93.0 | 56 |
| 13 | 0.450 | 81.1 | 59.5 | 0.47 | 98.6 | 70 | 85.7 | 51.0 | 3.26 | 98.4 | 70 |
| 14 | 0.450 | 86.4 | 61.7 | 1.30 | 98.9 | 76 | 90.5 | 48.9 | 4.47 | 98.6 | 76 |
| 15 | 0.550 | 84.1 | 38.3 | 4.55 | 98.0 | 42 | 89.6 | 29.2 | 11.04 | 98.3 | 44 |
| 16 | 0.592 | 78.0 | 53.6 | 0.62 | 97.5 | 57 | 71.1 | 62.2 | 3.71 | 96.0 | 55 |
| 17 | 0.463 | 42.6 | 73.3 | 0.84 | 87.4 | 72 | 43.4 | 73.4 | 1.25 | 84.9 | 71 |
| 18 | 0.500 | 81.0 | 45.0 | 4.39 | 97.0 | 51 | 86.3 | 41.5 | 8.55 | 98.0 | 51 |
| 19 | 0.450 | 76.8 | 55.5 | 2.80 | 96.4 | 48 | 80.1 | 50.9 | 6.44 | 97.1 | 49 |
| 20 | 0.400 | 79.2 | 52.1 | 4.73 | 97.7 | 57 | 76.9 | 53.6 | 5.36 | 96.6 | 55 |

Although differences between the measured results of the two algorithms are small, one trend is consistent: the percentage of contour points exceeding 250% of the prescription dose is smaller in every case for plans obtained from the branch-and-bound algorithm than for plans obtained via the genetic algorithm. This suggests that the former approach may provide better control on irradiation to external healthy tissue.

Figure 1N:
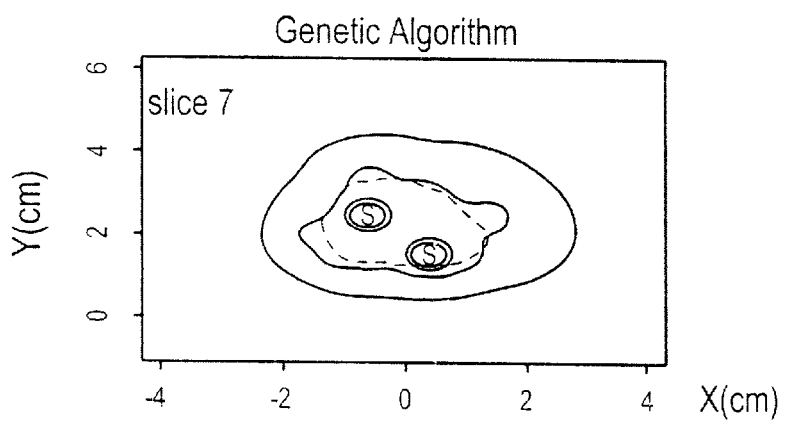

To visualize one instance of this, FIGS. 1a and 1n illustrate the isodose curves for Patient 8 for the branch-and-bound and genetic methods. In each frame of FIGS. 1a and 1n, the prostate contour is denoted by the dotted line, and the isodose curves for four distinct dose levels (0.5, 1.0, 1.5, and 2.0 times the prescription dose) are shown as solid lines. The character "S" is used to denote the position of a seed. FIGS. 1a–1n show the isodose curves associated with the plan obtained via the branch-and-bound algorithm, and FIGS. 1h–1n show the curves associated with the plan obtained via the genetic algorithm. Patient 8 provides an illustration of a trade-off that occurred in several cases: the percentage of contour points receiving 100% of the prescription dose is lower for the plan obtained from the branch-and-bound algorithm than for the plan obtained from the genetic algorithm (80% versus 93%), while the percentage of points receiving less than 115% of the prescription dose is higher for the plan obtained via the branch-and-bound algorithm (55% versus 38%). Again, this suggests that the branch-and-bound approach may provide better control on irradiation to healthy tissue. In both cases, the prescription isodose curves conform quite well to the prostate contours in slices 1–5 and less well in slices 6 and 7. However, careful inspection reveals that the prescription isodose curves in FIGS. 1a–1g conform slightly better than those in FIGS. 1h–1n. In addition, the areas enclosed by the 50% isodose curves are consistently smaller in FIGS. 1a–1g.

Figure 2A:
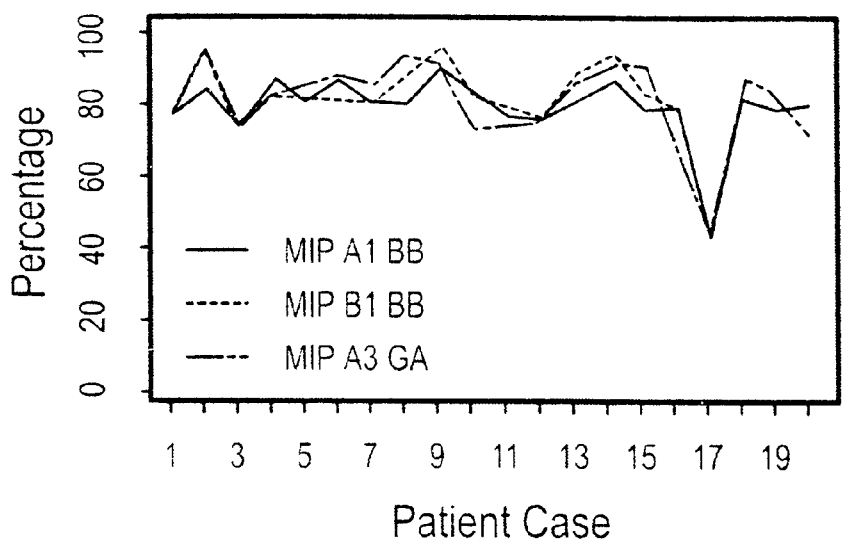
FIGS. 2a–2d are graphs showing the performance of various embodiments of brachytherapy treatment planning methods according to embodiments of the present inventions.
Figure 2B:
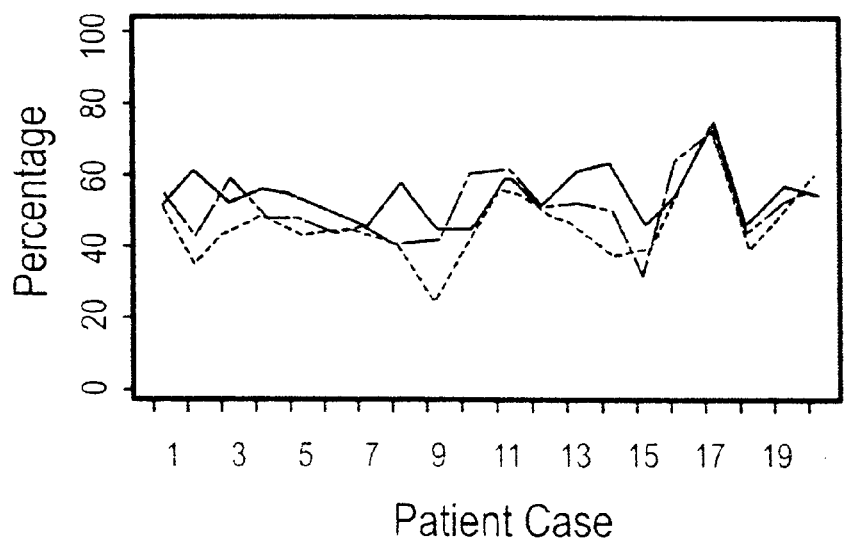
Figure 2C:
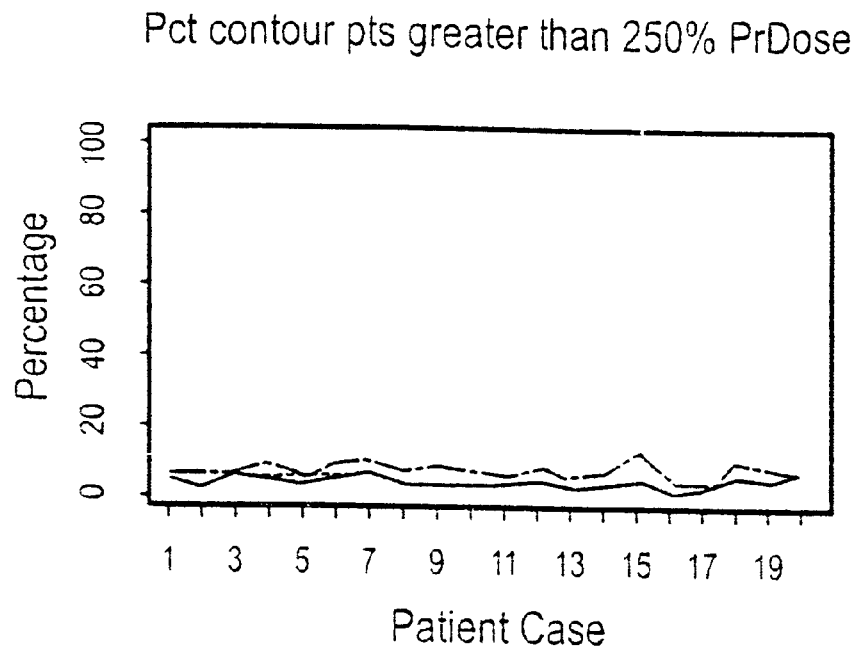
Figure 2D:
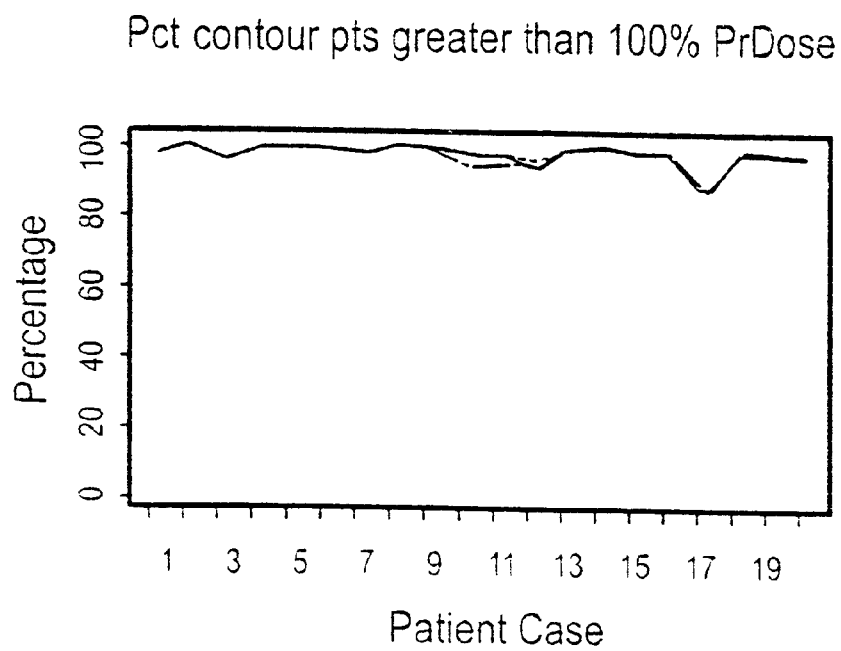
Figure 3:
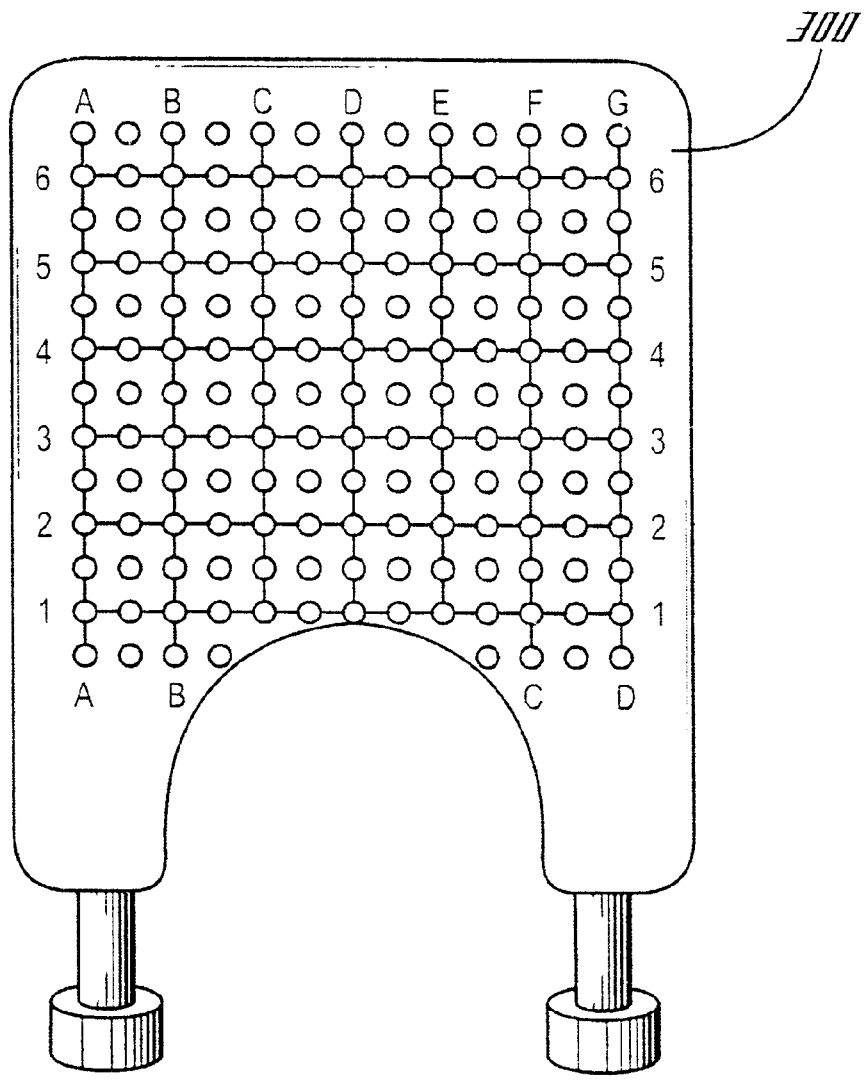
FIG. 3 is a front view of a needle template used in brachytherapy treatment.
Figure 4:
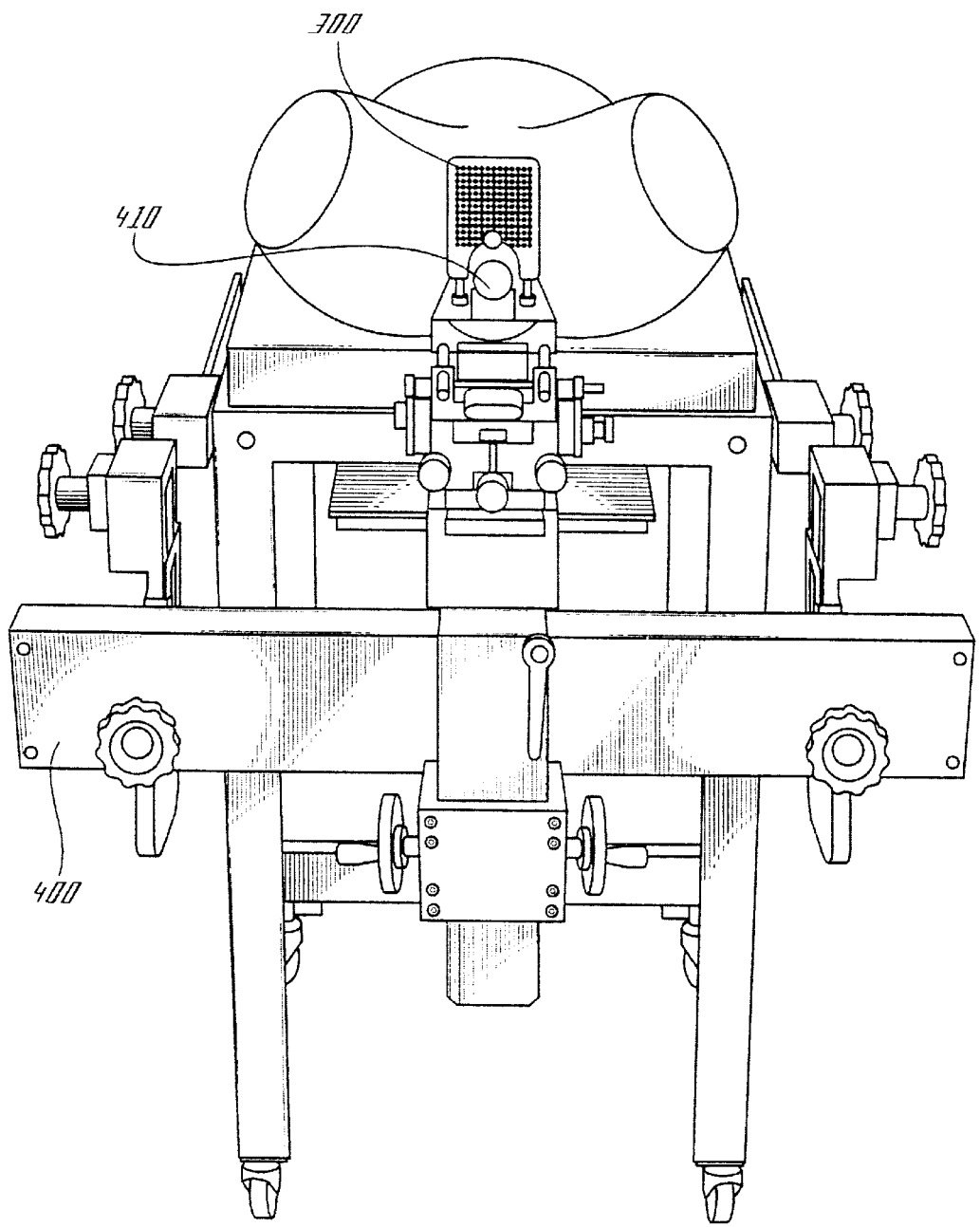
FIG. 4 is a front view of a transperineal implantation device with the template of FIG. 3.
Figure 5A:
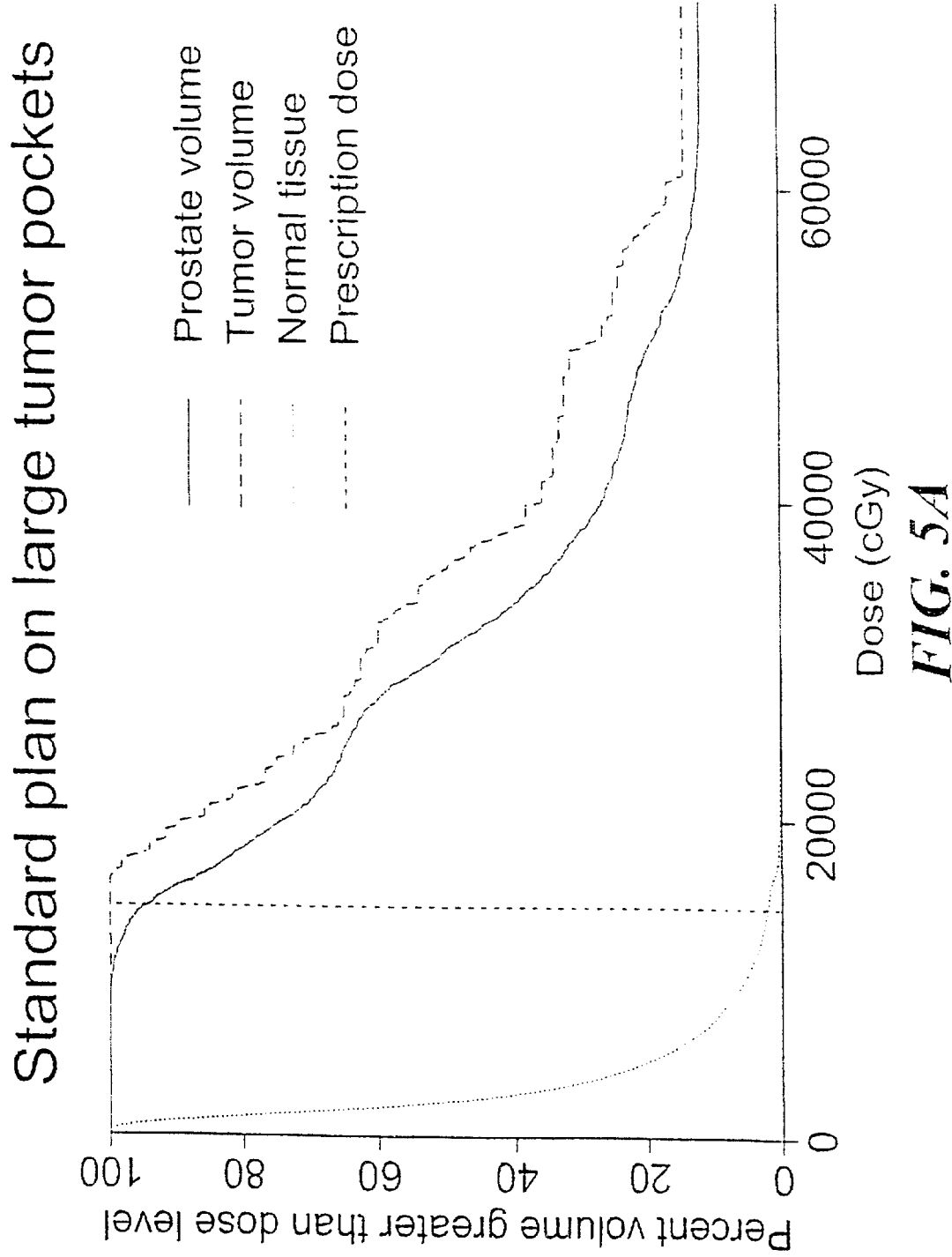
FIG. 5A is a histogram of volume per dose for several tissue types using non-conformal seeding treatment on a large tumor, according to one embodiment.
Figure 5B:
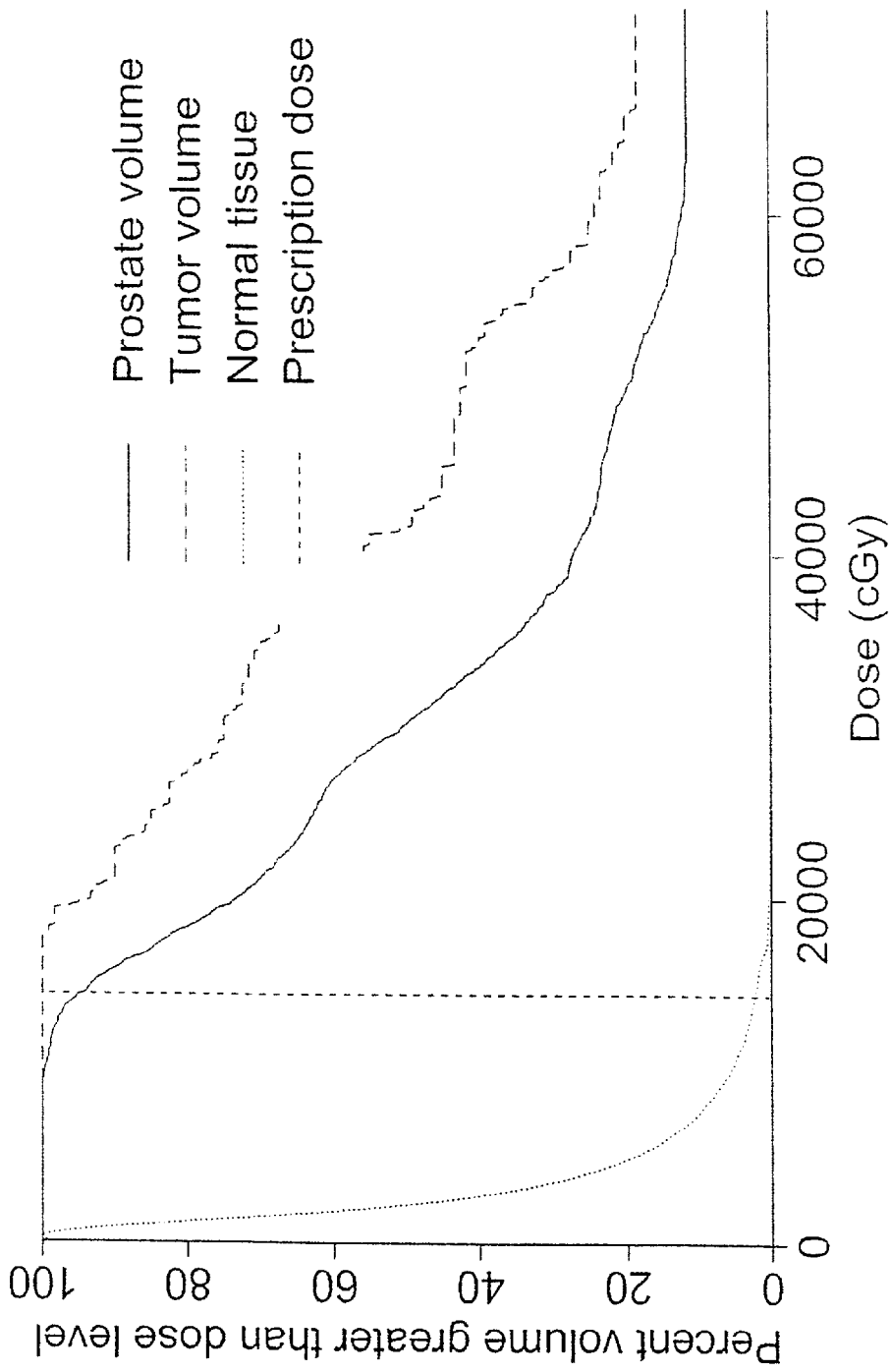
FIG. 5B is a histogram of volume per dose for several tissue types using conformal seeding treatment (MRS-guided) on a large tumor, according to another embodiment.
Figure 5C:
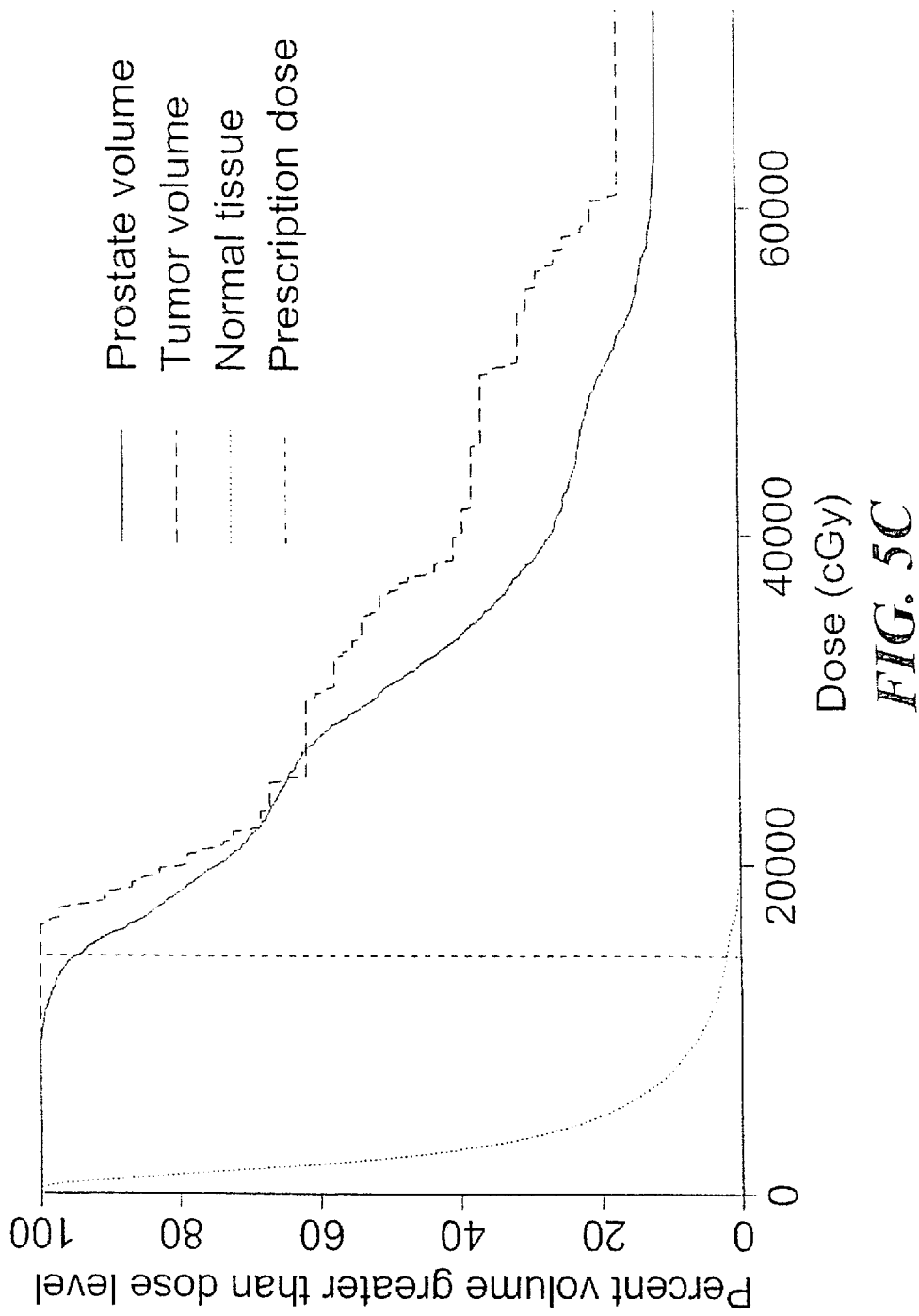
FIG. 5C is a histogram of volume per dose for several tissue types using non-conformal seeding treatment on a medium tumor, according to one embodiment.
Figure 5D:
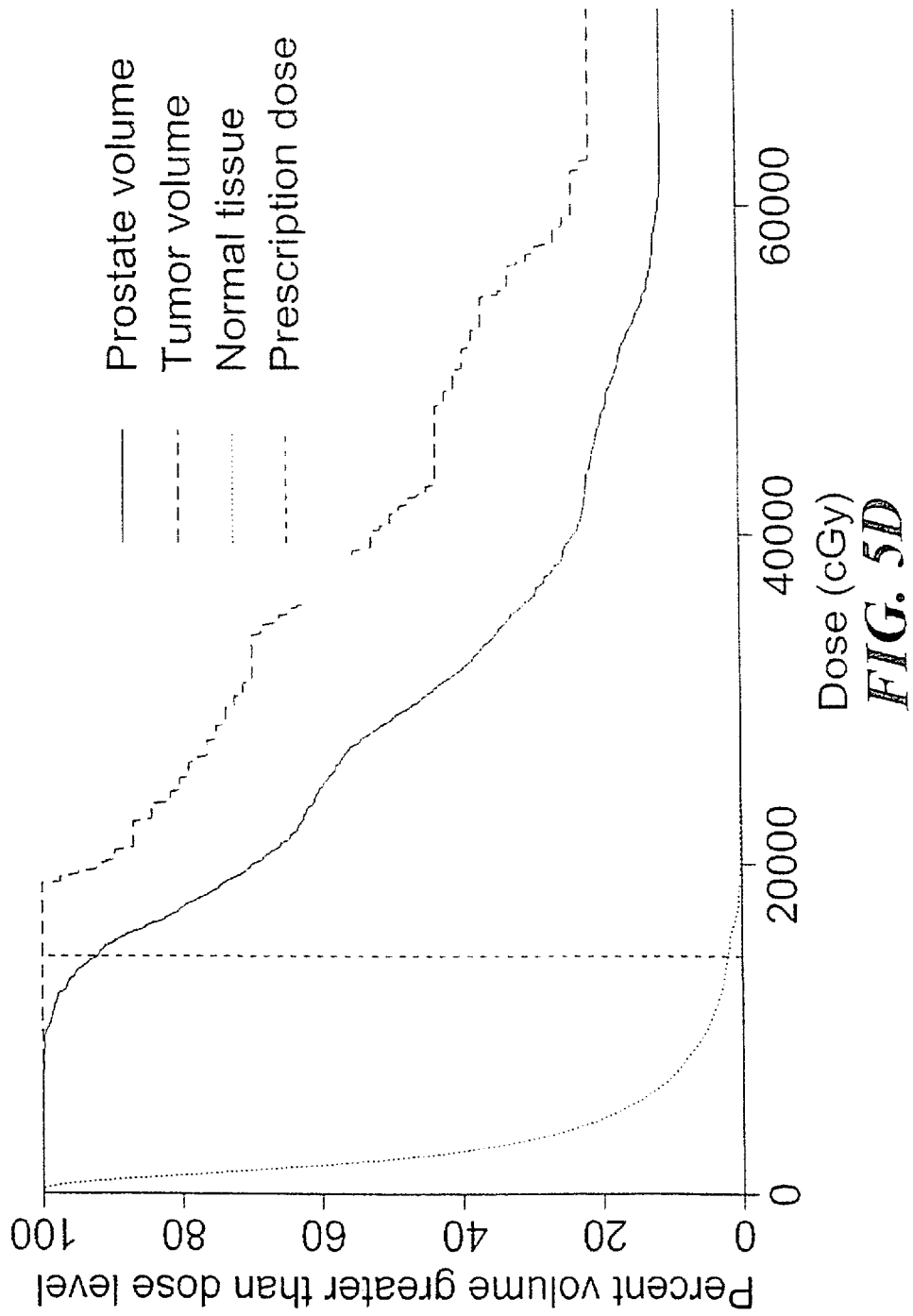
FIG. 5D is a histogram of volume per dose for several tissue types using conformal seeding treatment (MRS-guided) on a medium tumor, according to another embodiment.
Figure 5E:
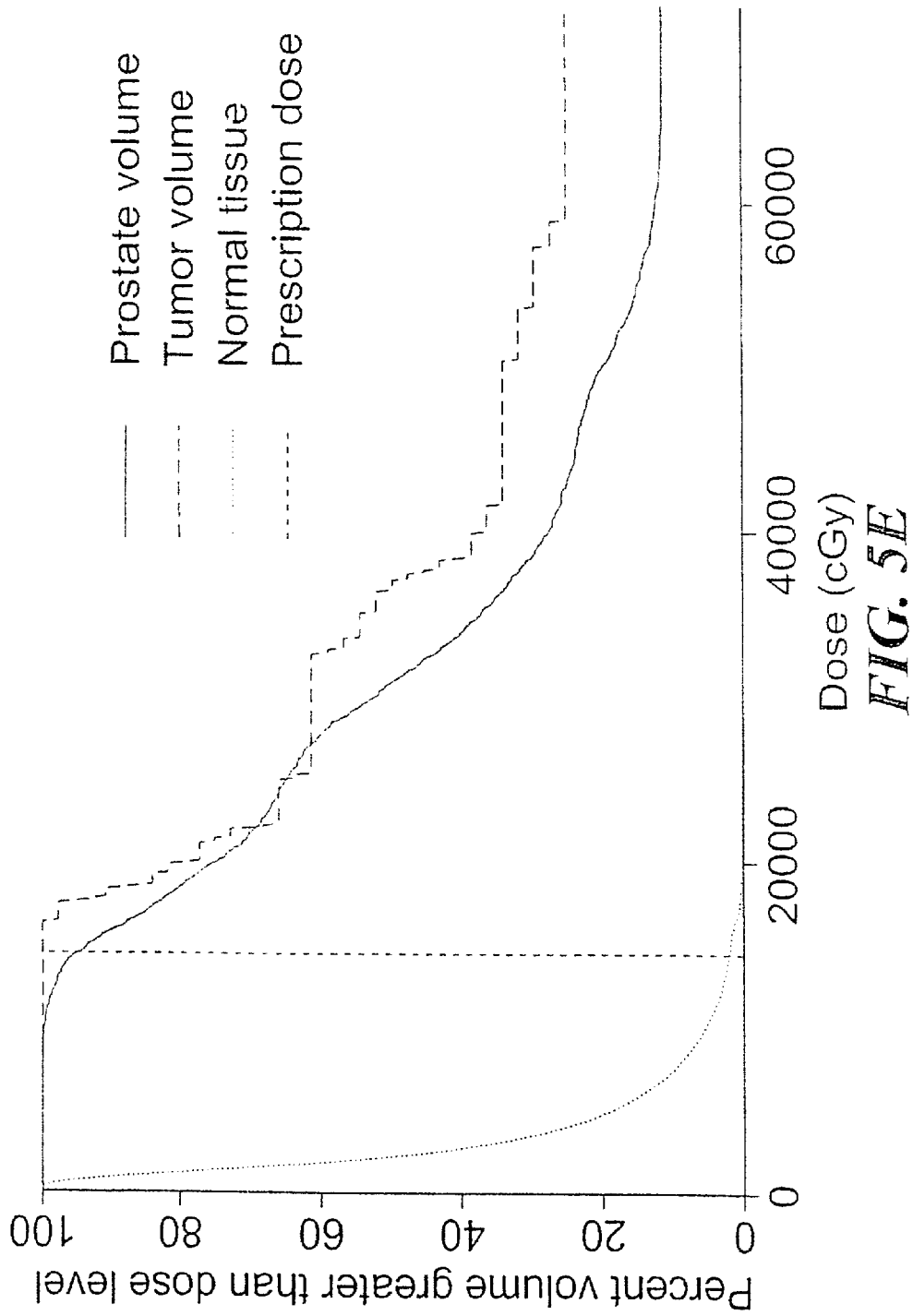
FIG. 5E is a histogram of volume per dose for several tissue types using non-conformal seeding treatment on a small tumor, according to one embodiment.
Figure 5F:
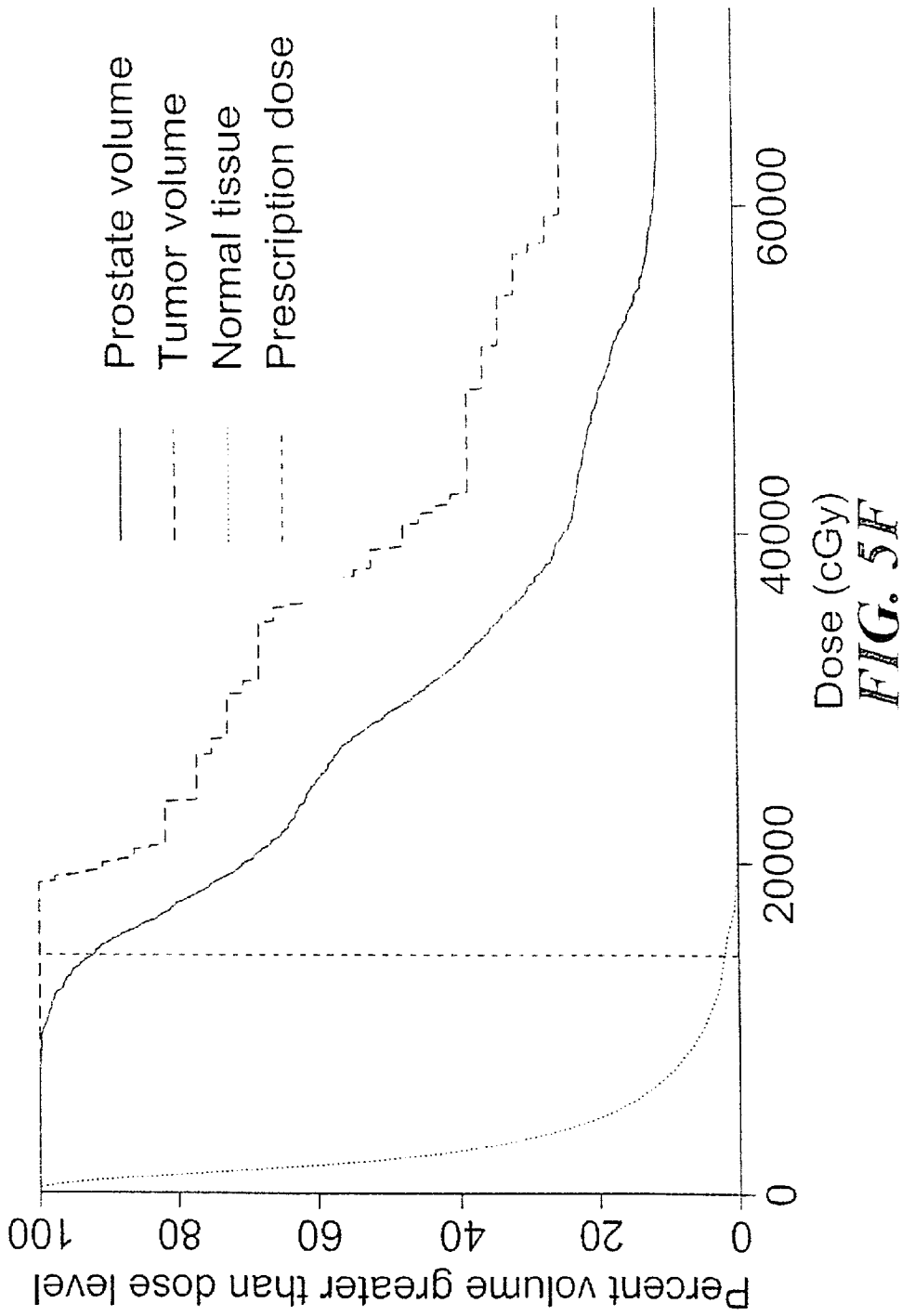
FIG. 5F is a histogram of volume per dose for several tissue types using conformal seeding treatment (MRS-guided) on a small tumor, according to another embodiment.

FIGS. 2a–2d provide a graphical view of some of the data displayed in Table 3, plus data from a third approach—branch-and-bound applied to (MIP B1). The fact that case 17 was difficult for all approaches stands out. Barring this one exception, FIG. 2d shows that all methods provided adequate coverage to the prostate—as measured by the percentage of uniformity points achieving at least 100% of the prescription dose (PrDose). It is also apparent from FIG. 2d that (MIP A3 GA) (the genetic algorithm applied to (MIP A3)) yields a consistently higher percentage of contour points with dose value exceeding 250% of the prescription dose than either of the other two methods. In contrast, from FIG. 2c, the percentage of contour points achieving a dose level less than 115% of the prescription dose was generally smallest for plans associated with (MIP B1 BB) (the branch-and-bound algorithm applied to (MIP B1)). These last two observations suggest that, among the three approaches, the gradient of the isodose contours associated with dose levels less than the prescription dose is generally steepest for (MIP A1 BB).

The mixed integer programming framework provides a very versatile environment for modeling brachytherapy treatment planning. The results of the numerical experiments presented herein show that this modeling paradigm coupled with appropriate optimization algorithms produce high-quality treatment plans in a fraction of the time (5–15 minutes) required by a human planner using traditional manual approaches (upwards of 4 hours). Although the results disclosed herein were not directly compared to those produced via manual approaches, based on the judgment of an experienced urologist and radiation oncologist, the computerized methods herein yield plans which use fewer seeds, provide better dose homogeneity within the target volume and lower irradiation to nearby external healthy tissue than plans obtained via manual methods.

Intensity-Modulated Conformal Treatment Planning Using Biological Imaging

Permanent implantation of radioactive seeds is becoming an increasingly popular treatment modality for early-stage prostate carcinoma. Typically, 60–150 radioactive seeds ($^{125}$I or $^{103}$Pd) are permanently implanted within the prostate in a specified geometric pattern to deliver a minimum peripheral dose of approximately 120–144 Gy. Transrectal ultrasound imaging (TRUS) can now be used to guide seed placement within the prostate, and real-time treatment planning algorithms are beginning to be used to determine the "ideal" seed placement within the prostate. True optimization of dose distributions, however, is still not possible because of uncertainties in tumor position within the prostate. This uncertainty forces the radiation oncologist to deliver maximum dose to the entire gland which in turn results (usually) in higher than optimum dose to the urethra. Unlike external-beam therapy, moderate (grade 2) urethral complications (e.g., urinary frequency and urgency necessitating medications for symptomatic relief) remain the single most important limitation in prostate implants, as it is often physically impossible to reduce the radiation dose to the urethra without compromising the dose distribution to the prostate. These side effects, while not severe, can have a significant impact on the patients' overall quality of life. While urinary side effects may be inevitable for patients treated with prostatic implantation, it is plausible that with improved optimization techniques and intra-operative correction protocols to further enhance needle distribution and seed placement, these side effects will be reduced without compromising local control.

Current implantation techniques do not incorporate some biological factors in the planning process. A recently developed rectal magnetic resonance (MR) coil now permits functional imaging of the prostate via MR spectroscopy (MRS). Localized MRS spectra can map citrate and choline concentrations within the prostate. In the peripheral zone the relative levels of these two compounds identify regions of prostate carcinoma with actively proliferating tumor cells. Currently, MRS images have spatial resolution of 6 mm, and this permits locating tumors to specific sites of the prostate. This information can be incorporated into real-time treatment planning calculations wherein radioactive seeds can preferentially be placed in regions of the prostate identified as tumor, without (needlessly) increasing dose to the urethra.

In this example we describe a treatment planning system used at our institution for implementing prostate implants using biological imaging. In designing this system several issues were considered:

a) The feasibility of designing a computerized planning system capable of generating treatment plans with localized escalated dose (hot spots) in identifiable tumor regions while maintaining a minimal urethral dose, b) The registration of MRS information to ultrasound images, and c) The biological significance of dose escalation: given that the dose inside the prostate is already larger than the prescription (peripheral) dose, does selectively increasing the dose in some volumes result in enhanced local control.

We illustrate the MRS-guided dose-escalation approach with an actual patient case, and compare—using a model of tumor control probability (TCP)—plans designed with or without the benefit of the MRS data. The MRS-guided approach is one example of intensity-modulated conformal treatment.

Example Intensity-Modulated Conformal Treatment

[1]H magnetic resonance spectroscopic imaging (MRSI) can provide a window on the metabolism in the prostate. The major metabolites observed in an in vivo proton NMR spectrum from the normal prostate peripheral zone are choline-containing compounds (3.21 ppm), creatine (3.02 ppm) and citrate (a doublet of doublets at 2.5–2.8 ppm). The choline (Cho) peak is comprised mainly of choline, phosphocholine and glycerophosphocholine. These compounds are constituents of membrane synthesis and degradation pathways and have been shown to be elevated in many malignancies. The creatine (Cr) peak is comprised of creatine and phosphocreatine. Citrate is synthesized, stored and secreted by glandular tissue in the prostate.

In attempting to characterize prostate tissue by NMR spectroscopy, localization of spectra to small volumes within the prostate is essentially due to spatial variations in metabolite levels within the normal zonal anatomy as well as those that arise due to cancer. The group at the Magnetic Resonance Science Center at the University of California at San Francisco (UCSF) has developed techniques for acquiring proton MRSI data from the prostate at high resolution (0.24 cm$^3$ voxels, 6.2 mm in-plane resolution) with excellent suppression of water and lipids.

In vivo NMR of the normal prostate has shown that the peripheral zone contains higher levels of citrate than the central gland. In prostate cancer, choline-containing compounds have been shown to be elevated while citrate is reduced in agreement with previous extract studies. The ratio of [Cho+Cr]/Cit was found to differentiate cancer from healthy peripheral zone tissue in all cases using a value of 0.86 (three standard deviations above the mean normal peripheral zone ratio) as the demarcation line. Using this criterion, recent retrospective studies have shown excellent agreement between $^1$H MRSI and step-section histopathology in localizing cancer to a sextant of the prostate.

Data were acquired as follows: Using a General Electric Signa 1.5 Tesla MR Scanner. Radiofrequency (RF) excitation was achieved by using the whole body birdcage resonator and the NMR signal was received using a 4 element phased array antenna (G.E. Medical Systems, Milwaukee, Wis.) combined with an expandable MRInnervu endorectal probe (Medrad Inc., Pittsburgh, Pa.) for high sensitivity. The endorectal probe is comprised of a single loop surface coil mounted inside an inflatable casing. The probe is lubricated with K-Y jelly and inserted by a staff radiologist into the rectum of the patient where it is inflated with 100 cc of air to ensure proper operation of the antenna as well as good positioning adjacent to the prostate.

Following positioning of the endorectal probe, sagittal T1-weighted scout images were acquired, followed by T1-weighted axial images (field of view (FOV) 14 cm, 5 mm slice thickness, 1 mm gap), T2-weighted axial images (FOV 14 cm, slice thickness 3 mm, gap 0), and T2-weighted coronal images over the prostate (FOV 17 cm, slice thickness 3 mm, gap 0). The pulse sequence program utilized for the spectroscopic acquisition utilizes the PRESS double spin echo technique to excite a rectangular volume containing the prostate. Prior to spectroscopic imaging, the water signal from the PRESS-excited volume is shimmed automatically with manual adjustment if necessary. Mapping of metabolites over a 50-cm field of view (FOV) is performed using chemical shift imaging (CSI) to encode $(6.25)^3$ mm$^3$ voxels. Suppression of water and lipid is performed using the BASING technique. The spectroscopic acquisition requires 17 minutes, whereas the full examination requires approximately one hour.

Following acquisition, images and spectral data were transferred to a Sun Ultrasparc Workstation (Sun Microsystems, Mountain View, Calif.) for processing. Processing of the spectral data includes 2 Hz Lorentzian apodization in the time domain followed by 4-dimensional Fourier transform and automated frequency, phase and baseline correction of each voxel using a combination of software routines. Data are zero-filled in the superior-inferior (z) dimension resulting in effective resolution of 3.1 mm. Peak areas of Cho, Cr and Cit are calculated by numerical integration over the spectral ranges corresponding to each metabolite. Peak areas and ratios of [Cho+Cr]/Cit are calculated and may be displayed as part of the spectral grid. Data are displayed overlaid on the corresponding T2-weighted images.

In an example of a MRSI data set acquired at this institution, the subject was previously untreated with a Gleason grade of 7 and a PSA level of 8 ng/ml. On the T2-weighted image, periprostatic lipids are bright, with normal central gland appearing hypointense to healthy peripheral zone. The peripheral zone in this image shows a darker region in the central, posterior aspect, which would be considered suspicious for cancer. Spectra were classified as "healthy" peripheral zone (H) if [Cho+Cr]/Cit<0.76, "suspicious for cancer" (SC) if 0.76<[Cho+Cr]/Cit≤0.86 or "very suspicious for cancer" (VC) if [Cho+Cr]/Cit>0.86. Spectra with poor metabolite signal-to-noise ratio or contamination by lipid were classified as non-diagnostic (ND). Voxels in the central gland were not assessed. Asterisks are used to indicate voxels comprised of mixed peripheral zone and central gland. From left to right in the lowest row of voxels, the spectra show a transition from healthy peripheral zone to suspicious.for cancer. The fifth voxel from the left in this row is labeled healthy strictly using the UCSF criteria; [Cho+Cr]/Cit was 0.7. Several peripheral zone voxels were considered nondiagnostic based on the low signal-to-noise ratio.

Registration of the MRS Information to Ultrasound Images

The MR images used for spectral analysis of the prostate are obtained with a rectal probe that is inflated to a total volume of about 100 cc. Under these conditions the prostate gland is pushed in the anterior direction against the pubic bone and thus assumes a slightly flattened shape. Since the implant procedure, and accompanying treatment planning, are based on the intraoperative ultrasound study where the prostate is uncompressed, it is important to devise a procedure for mapping points of interest from the MRS to the ultrasound (US) images.

Changes in the shape of the prostate volume during MR spectroscopy are indicated by two MR studies of the same patient—one with a body coil and the other with the rectal probe. We find that within a good approximation the total volume of the prostate remains constant. To map prostate voxels between the MR and US volumes we have assumed that points within the gland maintain the same relative position with respect to the axial contours of the prostate, and have no displacement in the superior-inferior direction. Thus, relative to the central axis of the gland (AB or A'B') the coordinates of point E in the US image corresponding to point E' in the MR volume are obtained using the following proportions:

$$f_1 = \frac{A'C'}{A'C'} = \frac{AC}{AB} \quad f_2 = \frac{C'E'}{C'D'} = \frac{CE}{CD} \quad (6)$$

The (approximate) validity of this scheme has been confirmed with an MR study of a patient who had previous seed implantation. It was thus possible to identify the same seeds in images of the normal-shaped and MR-deformed prostate and verify directly the applicability of the expression, Eq (6) above. We find that the ratios in Eq (6) agree within 7% (3 mm out of a 4-cm gland) which appears acceptable considering uncertainties in tumor detection (the MRS voxel size is 6×6×3 mm$^3$), prostate contours, seed placement and also seed migration post-implantation.

Optimization Planning System

The optimization module used in our treatment planning system uses the integer programming technique. Linear programming (LP) has been highly successful as a tool for external beam radiation treatment planning. It has only recently been explored as a viable tool for determining optimal seed placement in brachytherapy. The LP models that we have developed for treatment planning in prostate brachytherapy involve both discrete (0/1) and continuous variables. In general, such mixed-integer linear programs (MIPs) are more difficult to solve than their continuous counterparts. Although optimization software capable of solving general MIPs exists on the market, the biggest successes in solving real MIP instances have come from solvers tailored to the specific structure of the problem at hand.

Data for a patient include discretized representations of slices of the tumor site and neighboring healthy organs, and pre-specified target bounds for the dose. A grid of potential seed positions and exposure rate constants for the radioactive sources are also recorded during the actual implant procedure. Values of $L_P$ within the target are varied according to the tumor cell density as determined from MRS.

One possible approach is to identify a maximum feasible subsystem. This is the essence of our first model (MIP A). By introducing additional 0/1 variables to capture whether a constraint is satisfied or not, one can directly maximize the number of points satisfying the specified bounds. Clinically, this corresponds to maximizing the tumor volume satisfying the respective bounds. In practice, achieving the target bounds for certain points may be more critical than achieving the target bounds for certain other points. In this case, one maximizes a weighted sum, $\Sigma_P(\alpha_P v_P + \beta_P w_P)$, where the more critical points receive a relatively larger weight.

In another embodiment (MIPB) continuous variables are used to capture the deviations of the dose level at a given point from its target bounds and minimize a weighted sum of the deviations, such that:

$$\sum_{j=1}^{n} D(\|P - X_j\|) x_j + y_P \geq L_P \quad \sum_{j=1}^{n} D(\|P - X_j\|) x_j - z_P \leq U_P, \quad (7)$$

where $y_P$ and $z_P$ are non-negative, continuous variable.

In this model the values $U_P$ are obtained, as an example, from normal-tissue complication probability (NTCP) distributions. The objective for this model takes the form: minimize $\Sigma_P(\alpha_P y_P + \beta_P z_P)$, where $\alpha_P$ and $\beta_P$ are non-negative weights selected according to the relative importance of satisfying the associated bounds.

We note that the dose upper and lower bounds in constraints Eq(3) can be strategically set, using the experience from clinicians. Constraints for the tumor region (from MR images) have escalated lower bound and no upper bound; while the urethra has an upper bound and a lower bound which the clinicians consider necessary to eradicate microscopic traces of tumor cells.

We illustrate the MR-guided dose escalation approach via the automated planning system on an actual patient case. The prescription dose was 144 Gy using $^{125}$I seeds and the volume of the prostate was 38.1 cm$^3$. For the volume of the tumor region we have used three different values: 1.36, 2.35 and 3.71 cm$^3$ in order to verify (see next section) the sensitivity of the plan to this parameter. In each case the tumor was centered at the MRS-positive voxels. Bounds of 100% to 120% were imposed on the urethra. Bounds of 100% to 150% were placed on the uniformity points, and lower bound of 105% and no upper bound was placed on the tumor region. In two slices corresponding to the tumor location relative to the position of the urethra; the tumor volume is 1.36 cm$^2$. We clearly observe dose escalation around the tumor region in slice 1. In slice 2, where the tumor spot is in the vicinity of the urethra, the dose received by the urethra is kept within the strict pre-set levels and reasonable escalation is observed in the tumor area. Dose-volume histograms for the plans described above are shown in FIGS. 5A, 5B, 5C, 5D, 5E and 5F. The three curves in each graph correspond to: a) pockets of tumor identified via MRS, b) the rest of the prostate, and c) "healthy" tissue; this denotes tissue immediately outside the prostate as defined by the intersection of the prostate volume with a rectangular box that contains the prostate. For each tumor volume, the two sets of DVH curves represent, respectively, plans with or without dose escalation in the tumor pockets. Also indicated in the figures (vertical line) is the prescription dose. Notice that in both plans the curves for the normal tissue remain the same. For the escalated plan the dose in the remaining prostate is slightly lower; however in the pockets with tumor cells the dose is significantly larger than in the plan without dose escalation. A biological interpretation of these results is given below.

Table 4 shows the minimum and maximum dose in the urethra for plans calculated for the three tumor volumes considered above. Table 5 indicates, for each plan, the percentage of urethra volume in two dose ranges.

TABLE 4

Minimum and maximum doses in urethra (Gy); prescription dose: 144 Gy

| Tumor volume (cm$^3$) | Standard plan (Plan A) | | MRS-guided plan (Plan B) | |
|---|---|---|---|---|
| | Minimum dose | Maximum dose | Minimum dose | Maximum dose |
| 1.36 | 146.0 | 172.7 | 144.3 | 172.5 |
| 2.35 | 146.0 | 172.7 | 144.3 | 172.5 |
| 3.71 | 146.0 | 172.7 | 143.3 | 174.0 |

TABLE 5

Dose-volume distributions for urethra (percentage of volume in each dose interval) for the four plans discusses in the text.

| Dose interval (Gy) | MRS-guided plan | | | Standard plan |
|---|---|---|---|---|
| | 1.36 cm$^3$ | 2.35 cm$^2$ | 3.71 cm$^3$ | |
| 144–158.4 | 25% | 25% | 22.5% | 18.75% |
| 158.4–172.8 | 75% | 75% | 77.5% | 81.25% |

The Potential Biological Significance of MRS-Guided Treatment Planning

A typical tumor comprises a heterogeneous collection of cells of different radiosensitivity and/or cell proliferation kinetics. Nonetheless, it is generally understood that cells that are radioresistant and/or rapidly proliferating will control almost entirely its response to radiation treatment. In this sense, the tumor parameters used below are meant to represent this particular group. To the extent that MRS can be taken as a fingerprint for faster-proliferating tumor cells, recognizing regions with larger density of such cell populations could be consequential in terms of tumor local control. To examine this point, we compare below—using a series of hypothetical tumor parameters—the TCP for two optimized plans (same patient) designed to incorporate (plan B) or omit (plan A) the MRS information. Specifically, we are interested in: a) the maximal TCP gain obtainable by incorporating MRS information in treatment planning, and b) the largest fractional tumor volume for which MRS-guided planning remains useful (clearly, if tumor cells are uniformly spread throughout most of the prostate volume the gain would be insignificant).

For a tumor containing initially (before treatment, at time t=0) n tumor cells, the TCP is given by the following expression:

$$TCP(t) = \left[1 - \frac{S(t)e^{(b-d)t}}{1 + bS(t)e^{(b-d)t} \int_0^t \frac{dt'}{S(t')e^{(b-d)t'}}}\right]^n \quad (8)$$

Here S(t) is the survival probability at time t of tumor cells, and b and d are, respectively, the birth and death rates of these cells. Equivalently, $b=0.693/T_{Pot}$ and d/b is the cell loss factor ($\phi$) of the tumor. In this expression t refers to any time during or after the treatment; typically, one would take for t the end of the treatment period or the expected remaining life span of the patient. In practice, for permanent implants t would be made sufficiently large to satisfactorily approximate TCP($\infty$).

An actual calculation of TCP requires an explicit expression for S(t). For simplicity and convenience we shall use the linear-quadratic expression:

$$S(D) = e^{-\alpha D - \beta q(t) D^2} \quad (9)$$

where D is the total dose delivered up to time t, and thus a function of time. The function q(t) makes explicit the repair of sublethal damage. For a situation where the dose rate decreases exponentially:

$$q(t) = \frac{2(\lambda t)^2}{(\mu t)^2 (1-\lambda^2/\mu^2)(1-e^{-\lambda t})^2} \left[e^{-(\lambda+\mu)t} + \mu t\left(\frac{1-e^{-2\lambda t}}{2\lambda t}\right) - \frac{1+e^{-2\lambda t}}{2}\right] \quad (10)$$

$\gamma$ is the radioactive decay constant of the radioisotope (e.g. for $^{125}$I it is $1.152 \cdot 10^{-2}$ d$^{-1}$) and $\mu=1/t_0$, where $t_0$ is the average time for the sublethal damage repair, typically of the order of one hour. Taking the product of TCP values for groups of cells exposed to the same dose accounts for dose inhomogeneity in the tumor.

The six parameters needed in this calculation are: $\alpha$, $\beta$, $t_0$, $T_{Pot}(=0.693/b)$, $\phi(=d/b)$ and n. Other than n, it is of course quite unlikely that any particular tumor will contain cells that have unique values of these quantities. As already indicated, the numbers used hereinafter for evaluating the TCP should be taken to represent the response of the fast-proliferating and/or radioresistant segment of tumor cells. A justification of the numerical values selected for these parameters is now given.

For $\alpha$ and $\beta$ we have used values determined from in vitro cell survival measurements; of the two lines of prostate tumor cells studied, one radiosensitive ($\alpha=0.487$ Gy$^{-1}$, $\beta=0.055$ Gy$^{-2}$) and the other radioresistant ($\alpha=0.155$ Gy$^{-1}$, $\beta=0.052$ Gy$^{-2}$) we have selected the latter one. A recent publication reports cell kinetic measurements for prostate cancer cells: for five different tumors the potential doubling time, $T_{Pot}$, was found to vary between 16 and 61 days and we take here $T_{Pot}=16$ d. The same report estimates the cell loss factor to $\phi=0.75$. For the sublethal damage repair constant we take $t_0=1$ h, in line with numerous experimental determinations of this quantity; the precise choice of this quantity is not critical because for these forms of treatment TCP is rather insensitive to changes in $t_0$.

The determination of the number of clonogenic cells in a tumor remains a matter of controversy. Several methods have been suggested, for instance using the normalized dose gradient $\gamma$, but generally the numbers thus obtained appear rather unrealistic. For prostate, the following formula for calculating the volume, V, of prostate cancer cells has been suggested:

$$V_{cm^2} = \frac{PSA_{ng/ml} - (0.2)(0.33)(PV_{cm^3})}{PSAL_{ng\ cm^3/ml}} \quad (11)$$

Here PSA is the amount of prostate specific antigen, PV is the prostate volume as determined, for instance, by transrectal ultrasound, and PSAL is the PSA leak into the serum (ng/ml) per unit volume (cm$^3$) of cancer cells. The denominator in Eq(11) represents cancer-specific PSA, that is PSA corrected for the contribution of benign epithelial cells; 0.2 is the estimated fraction of epithelial cells and 0.33 is their corresponding PSAL. A paper reports PSAL values as a function of Gleason score, G. We have fitted these values to the following empirical equation:

$$PSAL_{ng\ cm^3/ml} = 42.3\exp(-0.749G) \quad (12)$$

With this, the number of cancer cells is $n=\rho V$, where $\rho$ is the volume density of cells in the prostate tumor; here we take $\rho=10^9$ cells/cm$^3$. Using Eqs(11, 12), the three tumor volumes considered below (1.36, 2.35, 3.71 cc) can be taken to represent, for instance, a patient with G=5 and PSA=3.6, 4.6 and 6.0 ng/ml, respectively. There are, of course, other PSA-G combinations that lead to the same values of V.

In Table 6 we compare TCP for MRS-guided and standard plans. These results were obtained by assuming that: a) all radioresistant tumor cells are located in the MRS-positive volumes and b) other tumor cells do not affect significantly the TCP. Without assumption (b), the numbers given in Table 6 are only upper limits of the actual TCP values. Thus, for this particular set of parameters and for this patient, Table 6 gives the maximum gain obtainable with MRS-guided planning.

TABLE 6

Estimated TCP values
(n = 1.36 10$^9$ cells, PV = 38.1 cm$^3$)

| Tumor volume (cm$^3$) | Standard plan (Plan A) | MRS-guided plan (Plan B) | Ratio of Plan B to Plan A |
|---|---|---|---|
| 1.36 | 0.649 | 0.943 | 1.45 |
| 2.35 | 0.650 | 0.965 | 1.48 |
| 3.71 | 0.761 | 0.948 | 1.25 |

The MRS-guided treatment plan appears consistently (and significantly) superior to the standard plan. As anticipated, as the tumor volume increases the difference between the two plans shrinks.

$TCP_i$ for individual subgroups of cells, i, treated each at the same dose, $D_i$, indicates that the final TCP $$\left(\text{which is equal to } \prod_i TCP_i\right)$$

is essentially determined by contributions from the lowest dose bins. This makes makes the point that treatment-plan optimization must focus on increasing the lower dose threshold in tumor-containing voxels rather than on the overall shape of the dose-volume distributions. It also emphasizes the need for accurate seed positioning in prostate implants.

This treatment planning system for prostate implants makes use of biological imaging. In a typical implant the dose delivered to the gland is equal to or larger than the is prescription isodose, which is usually meant to cover the periphery of the prostate. The dose distribution inside the prostate is highly non-uniform. There is enough justification to intentionally place the (inevitable) hot spots of the plan in regions potentially known to contain pockets of radioresistant tumor cells. Plans that have the same prostate coverage by the prescription isodose are not necessarily "the same". To the extent that MRS can detect fast-proliferating tumor cells, using "reasonable" radiobiological parameters and a TCP model, incorporating this information in the treatment planning process may lead to substantial improvements (e.g. 45%) in local control. The magnitude of the TCP enhancement, and therefore the risks of ignoring the MR data, appear to be more substantial when the tumor is well localized. The disclosed optimization algorithm is capable of escalating the dose in individual voxels without affecting the healthy tissue surrounding the prostate and the urethral dose.

It is an advantage of MR-guided treatments to allow the possibility of dose de-escalation away from tumors, thus reducing toxicity in adjacent healthy tissues.

Determining an Effective Planning Volume for Permanent Prostate Implants

When planning a brachytherapy prostate implant, the planning target volume (PTV) for the prostate is typically based on a medical image taken during a simulation session several days prior to the implantation. Unfortunately, since the prostate at the time of implantation is often swollen (due to the insertion of needles) the pre-implant PTV may not provide an accurate representation of the prostate at implant time. Hence, a plan based on the pre-implant PTV, however well designed, may not provide the desired dosimetry for effectively treating the diseased prostate.

As sophisticated computerized optimization algorithms become more integrated into treatment planning systems, the need to design plans days in advance of implantation will diminish, and planning will likely occur immediately prior to implantation. In particular, it is reasonable to design plans based on the swollen prostate. Nevertheless, by itself, the merging of the planning process with the implantation procedure may not provide improved dosimetry to the prostate. A plan based on the swollen prostate volume may conform well to the swollen prostate, but it may not provide good dosimetry over time as shrinkage occurs.

Motivated by the fact that post-implant seed movement and prostate swelling and shrinkage inevitably occur, we investigate herein the problem of determining an "effective planning target volume" (EPTV) for permanent implants in prostate cancer treatment planning. In particular, we investigate the possibility of utilizing projected target volumes at later times to assist in the planning process.

The effect of edema associated with prostate implants has been reported. In particular, Waterman et al. (Waterman F M, Dicker A P. Effect of post-implant edema on the rectal dose in prostate brachytherapy, *International Journal of Radiation Oncology and Biological Physics*, 1999; 45:571–576) described the duration and magnitude of edema via an analysis based on serial CT scans. If $V_0$ denotes the prostate volume immediately after implantation, then the prostate volume at time t, $V_t$, after implantation can be approximated by the formulation $$V_t = V_0[1 + \Delta V(e^{-0.693t/T} - 1)], \qquad (13)$$

where $\Delta V$ is the initial relative increase of the edema, and T is the half-life of edema decay.

We propose and analyze single-period and multi-period time-dependent dosimetric treatment planning models spanning a period of thirty days. In particular, the target volume at day 0 (swollen prostate) and projected target volumes at days 6, 12, 18, 24 and 30 (based on Eq (12)) are used in formulating the models. Corresponding to each model, an optimal treatment plan is obtained via an automated planning system. The dosimetric coverage and conformity over a period of thirty days are then compared. Based on the comparison study, we gain insight into how one might arrive at an effective planning target volume—a volume upon which the initial planning configuration should be determined.

Let t be the time from the initial implantation; and let P(t) denote the target prostate, D(t) the dose that remains to be absorbed, and S(t) the potential seed positions at time t. The initial values, P(0), D(0) and S(0), correspond, respectively, to the initial (swollen) prostate after insertion of needles, the prescription dose specified by the clinician, and the initial potential seed positions. To approximate the shrinkage of the edema and seed displacement, we assume for the purposes of this study that the edema volume at time 0 is 1.414 times the size of the "normal" volume of the prostate, and that shrinkage occurs uniformly towards a point source specified as the center of mass of the swollen prostate at time 0. Based on this assumption, each linear dimension at time 0 is scaled by the cubic root of this volume change (1.122), and the position of a point source at time t along a single dimension is approximated by the equation $$TD(P) = \sum_{j=1}^{n} D(\|P - X_j\|)x_j \qquad (14)$$

where $x_0$ is the coordinate along the given dimension of the point source at time 0, $x^c$ is the associated coordinate for the center of mass at time 0, and T is the half-life of edema decay. (For this example, we assume the half-life of edema decay is 15 days.) Since the movement of implanted seeds are affected by the movement of cells and tissues inside the prostate, it is reasonable to assume that seed movement also approximately follows the linear reduction given by equation (14).

For both the single-period and multi-period treatment planning models, we focused on a 30 day time horizon, and considered six specific points in time: t=0, 6, 12, 18, 24, 30 days. For the single-period model, for each of the specified times, a treatment plan was derived based on the projected volume and seed positions at that time. (The automated treatment planning system used to derive the treatment plans is described above) Once derived, the dosimetry associated with a plan was measured at all of the six specified times (t=0, 6, 12, 18, 24, 30); at each time taking into account the projected shrinkage of the prostate and shifting of seeds.

The idea of a multi-period model is to consider more than a single time period when deriving a plan. For the study described herein, dosimetric constraints to assist in obtaining conformal prescription isodose curves at mutliple time periods were imposed. A treatment plan was then designed (again using the system described above) to satisfy the maximum number of dosimetric constraints across the multi-period time horizon. Specifically, we considered five two-period models. For each model, dosimetric constraints based on time 0 and time t were imposed, where t=6, 12, 18, 24, 30. As with the single-period models, dosimetry measures (coverage and conformity) resulting from each plan were analyzed over the thirty day horizon.

Dosage Variations with Time

Two criteria were used to measure the quality of the resulting plans. Conformity at time t is computed as the ratio of the total volume enclosed by the isodose surface D(t) to the target volume enclosed by this same surface. Coverage at time t is computed as the ratio of the target volume enclosed by D(t) to the total target volume. Hence, a conformity index is always greater than or equal to 1, and a coverage index is always less than or equal to 1. In either case, an index value of 1 indicates perfect conformity/coverage.

Tables 7 and 8 summarize the results for the single-period model. Each column gives the mean, maximum and minimum of the conformity (coverage) indices at times 0, 6, 12, 18, 24, 30 for the plan generated from the data specified by $P(t_1)$, $D(t_1)$ and $S(t_1)$.

TABLE 7

Conformity statistics for 30 day time horizon
using single-period model plan based on $P(t_1)$, $D(t_1)$, $S(t_1)$, $t_1 =$

| | statistic | | | | | |
|---|---|---|---|---|---|---|
| | 0 | 6 | 12 | 18 | 24 | 30 |
| mean | 1.2692 | 1.2223 | 1.1743 | 1.1538 | 1.1289 | 1.1193 |
| max | 1.3649 | 1.3060 | 1.2505 | 1.2271 | 1.1928 | 1.1767 |
| min | 1.141 | 1.1192 | 1.0876 | 1.0730 | 1.0579 | 1.0557 |

TABLE 8

Coverage statistics for 30 day time horizon
using single-period model plan based on $P(t_1)$, $D(t_1)$, $S(t_1)$, $t_1$,

| | statistic | | | | | |
|---|---|---|---|---|---|---|
| | 0 | 6 | 12 | 18 | 24 | 30 |
| mean | 0.9963 | 0.9786 | 0.9769 | 0.9610 | 0.9583 | 0.9557 |
| max | 0.9990 | 0.9962 | 0.9956 | 0.9828 | 0.9835 | 0.9813 |
| min | 0.9890 | 0.9358 | 0.9317 | 0.9314 | 0.9310 | 0.9310 |

Figure 6A:
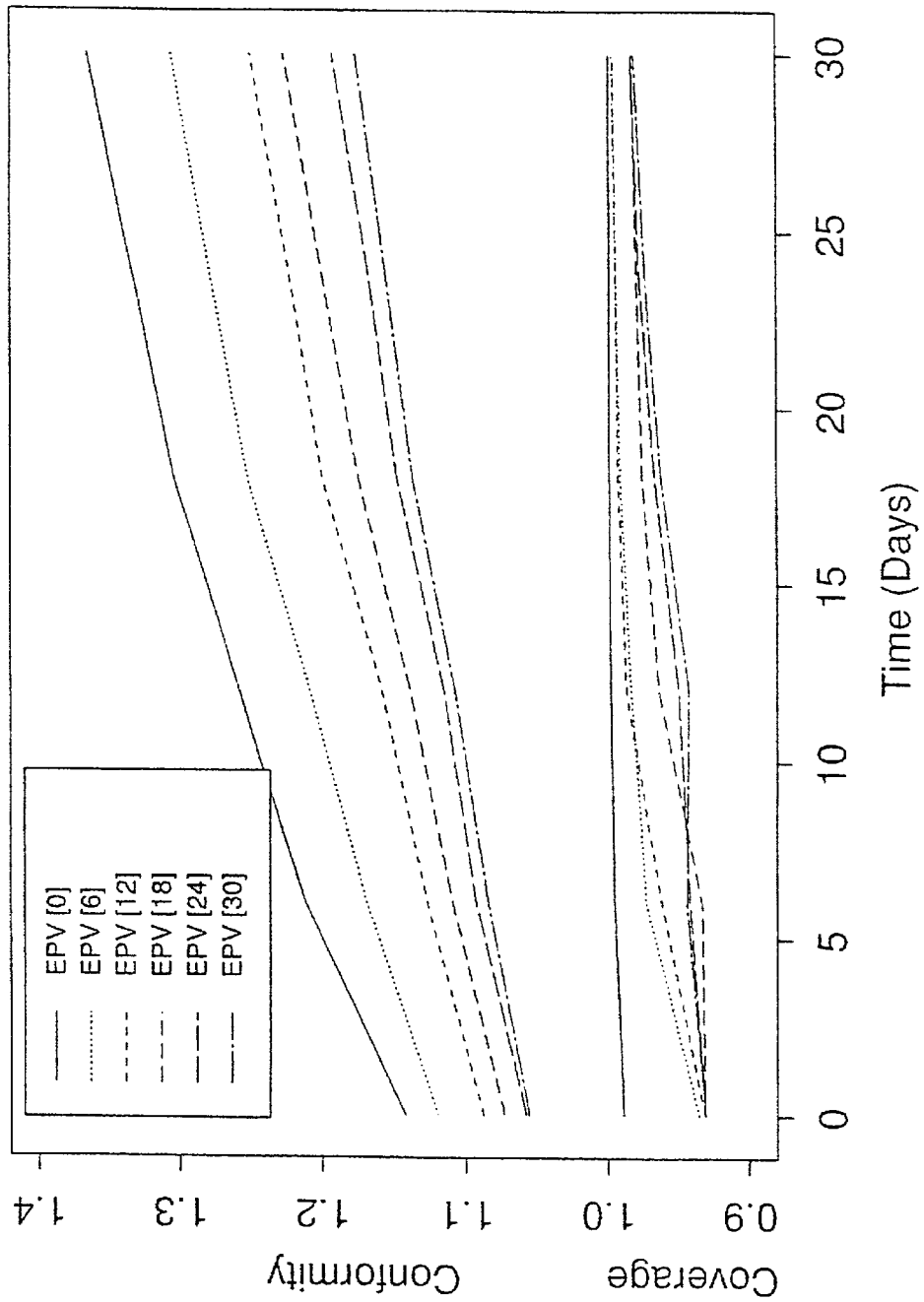
FIG. 6A is a graph showing coverage (<1) and conformity (>1) ratios for an effective planning volume based on a single period according to one embodiment.

Note that in both tables a consistent trend is apparent: as $t_1$ increases, both the conformity and coverage statistics decrease. In particular, the best coverage and the worst conformity is achieved when $t_1=0$; and conversely, the worst coverage and best conformity is achieved when $t_1=30$. Plans based on the initial data at $t_1=0$ provide over 99% coverage at all times, but have conformity indices reaching as high as 1.36. Plans based on projected data at $t_1=24$ and $t_1=30$ yield over 93% coverage, while maintaining conformity indices less than 1.2 over the entire 30 day period. FIG. 6A shows a plot of coverage and conformity indices for the six plans over a period of 30 days. We notice that the initial prostate volume after needle insertion induces the highest normal tissue irradiation over a period of 30 days.

Figure 6B:
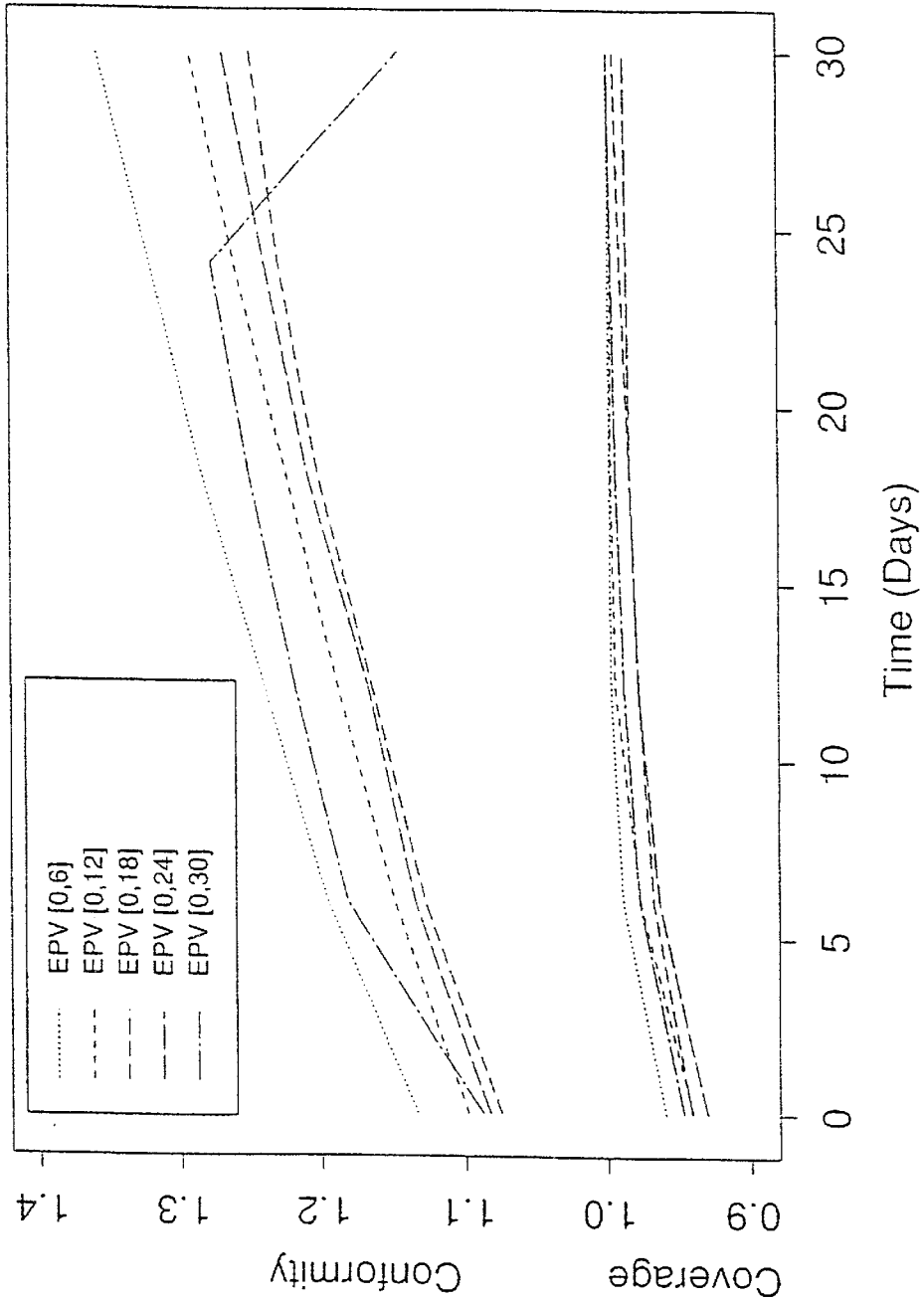
FIG. 6B is a graph showing coverage (<1) and conformity (>1) ratios for an effective planning volume based on two periods according to another embodiment.

Tables 9 and 10 and FIG. 6B summarize the results for the two-period model. Compared to FIG. 6A, the overall coverage for the two-period plans over the 30 day horizon are uniformly better than those obtained from the single-period plans (comparing corresponding values for $t_1$). For $t_1=6$ and $t_1=12$ the conformity results are only marginally different than the corresponding single-period results. However, the results are more mixed for larger values of $t_1$. For instance, FIG. 6B illustrates that for $t_1=30$, the conformity index dips at t=30. This is, of course, due to the fact that the model for $t_1=30$ is emphasizing conformity on day 0 as well as day 30. However, we also notice significant improvement in the coverage for this plan over the 30 day horizon.

TABLE 9

Conformity statistics for 30 day time horizon using two-period model plan
based on P(0), D(0), S(0) and $P(t_1)$, $D(t_1)$, $S(t_1)$, $t_1 =$

| | statistic | | | | |
|---|---|---|---|---|---|
| | 6 | 12 | 18 | 24 | 30 |
| mean | 1.2554 | 1.2022 | 1.1747 | 1.1839 | 1.1936 |
| max | 1.3581 | 1.2923 | 1.2494 | 1.2692 | 1.2776 |
| min | 1.1335 | 1.0986 | 1.0759 | 1.0837 | 1.0884 |

TABLE 10

Coverage statistics for 30 day time horizon using t1 wcperiod model plan
based on P(0), D(0), S(0) and $P(t_1)$, $D(t_1)$, $S(t_1)$, $t_1 =$

| | statistic | | | | |
|---|---|---|---|---|---|
| | 6 | 12 | 18 | 24 | 30 |
| mean | 0.9902 | 0.9840 | 0.9758 | 0.9715 | 0.9834 |
| max | 0.9992 | 0.9992 | 0.9946 | 0.9876 | 0.9992 |
| min | 0.9595 | 0.9402 | 0.9408 | 0.9305 | 0.9466 |

The results reported here demonstrate that a planning method embodiments that takes into account prostate shrinkage and seed displacement over time can be used to fine-tune the balance between coverage and conformity. In particular, if achieving good conformity is the higher priority it may be desirable to prepare a treatment plan embodiment based on the projected prostate volume at a later time.

Conclusion

While the invention has been described in detail in connection with the preferred embodiments known at the time, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Accordingly, the invention is not to be seen as limited by the foregoing description, but is only limited by the scope of the appended claims.

What is claimed is:

1. A method for planning the placement of seeds for a brachytherapy treatment of diseased tissue, the method comprising the steps of:

representing a placement or non-placement of a seed in each point of a predetermined three dimensional grid of potential seed locations with a binary indicator variable;

representing a tumor and surrounding tissue as a predetermined three dimensional tissue grid having a plurality of tissue points;

associating at least one of an upper bound and a lower bound for a dose of radiation received with each point in the tissue grid;

calculating an objective value based on a difference at each point of the tissue grid between an amount of radiation based on a trial placement of seeds and the at least one of the upper bound and the lower bound;

varying the trial placement of seeds and repeating the step of calculating the objective value, resulting in additional objective values;

selecting an optimal objective value from the calculated objective value and the additional objective values; and setting a planned placement of seeds based on the trial placement of seeds that obtains the optimal objective value.

2. The method of claim 1, wherein each tissue point is associated with one tissue type of a plurality of tissue types.

3. The method of claim 1, wherein
a first tissue type of the plurality of tissue types is based on a first image formed by a first imaging device; and
a second tissue type of the plurality of tissue types is based on a second image formed by a second imaging device.

4. The method of claim 3, the step of representing a tumor and surrounding tissue further comprising the step of mapping a point in the second image to a corresponding point in the tissue grid.

5. The method of claim 4, the step of mapping further comprising
determining a common tissue type apparent in images from the first imaging device and the second imaging device;
measuring a scaling distance along an axis from a center of the common tissue type to an edge of the common tissue type; and
computing a corresponding coordinate in the tissue grid based on a ratio obtained by dividing the scaling distance into a distance from the center to a coordinate of the point on the axis.

6. The method of claim 3, wherein
the first imaging device is an ultrasound imaging device; and
the second imaging device is a magnetic resonance spectroscopic imaging device.

7. The method of claim 3, wherein
the first tissue type is associated with undifferentiated normal tissue and cancerous tissue; and
the second tissue type is associated with cancerous tissue.

8. The method of claim 1, the step of representing a tumor and surrounding tissue based on biological imaging.

9. The method of claim 1, wherein the tissue grid represents the tumor and surrounding tissue at a particular time.

10. The method of claim 9, further comprising mapping the three dimensional grid of potential seed locations at a time of seed insertion to a new grid of potential seed locations at the particular time.

11. The method of claim 10, the method further comprising determining the particular time associated with an effective planning target volume based on variations in a conformity ratio over time, the conformity ratio at a certain time determined by dividing a target volume to be enclosed by an isodose surface into a volume enclosed by that surface at the certain time.

12. The method of claim 10, the method further comprising determining the particular time associated with an effective planning target volume based on variations in a coverage ratio over time, the coverage ratio at a certain time determined by dividing a total target volume into a volume enclosed by an isodose surface at the certain time.

13. The method of claim 9, wherein the particular time is an imaging time when an imaging device is used to form an image of the tumor and surrounding tissue.

14. The method of claim 9, wherein:
the method further comprises
mapping the tissue grid to a second tissue grid at a second time, and
mapping the three dimensional grid of potential seed locations at a time of seed insertion to a second grid of potential seed locations at the second time,
calculating a second objective value based on a second difference at each point of the second tissue grid at the second time, and
varying the trial placement to obtain a second optimal value at the second time; and
in step of setting the planned placement of seeds is further based on the trial placement that obtains the second optimal value.

15. The method of claim 9, wherein:
the method further comprises
mapping the tissue grid to a second tissue grid at a second time, and
mapping the three dimensional grid of potential seed locations at a time of seed insertion to a second grid of potential seed locations at the second time; and
the step of calculating the objective value is further based on second differences at each point of the second tissue grid between a second amount of radiation based on the trial placement of seeds mapped to the second grid at the second time.

16. A method for planning the placement of seeds for a brachytherapy treatment of diseased tissue, the method comprising the steps of:
representing a placement or non-placement of a seed in each point of a predetermined three dimensional grid of potential seed locations with a binary indicator variable;

representing a tumor and surrounding tissue as a predetermined three dimensional tissue grid having a plurality of tissue points;

wherein each tissue point is associated with one tissue type of a plurality of tissue types;

wherein a first tissue type of the plurality of tissue types is associated with slowly proliferating tumor cells;

wherein a second tissue type of the plurality of tissue types is associated with rapidly proliferating tumor cells;

associating at least one of an upper bound and a lower bound for a dose of radiation received with each tissue point in the tissue grid;

calculating an objective value based on a difference at each point of the tissue grid between an amount of radiation based on a trial placement of seeds and the at least one of the upper bound and the lower bound;

varying the trial placement of seeds and repeating the step of calculating the objective value, resulting in additional objective values;

selecting an optimal objective value from the calculated objective value and the additional objective values; and setting a planned placement of seeds based on the trial placement of seed that obtains the optimal objective value.

17. The method of claim 16, the step of associating at least one of the upper bound and the lower bound further comprising:
   determining whether the second tissue type is associated with a particular point in the tissue grid; and
   if it is determined that the second tissue type is associate with the particular point, then associating no upper bound with the particular point.

18. The method of claim 16, the step of associating at least one of the upper bound and the lower bound further comprising:
   determining whether the second tissue type is associated with a particular point in the tissue grid; and
   if it is determined that the second tissue type is associate with the particular point, then associating a particular lower bound with the particular point, the particular lower bound greater than a prescription dose allowed for healthy tissue.

19. The method of claim 16, the step of associating at least one of the upper bound and the lower bound further comprising:
   determining whether the first tissue type is associated with a particular point in the tissue grid; and
   if it is determined that the first tissue type is associated with the particular point, then associating a particular lower bound with the particular point, the particular lower bound substantially equal to a prescription dose allowed for healthy tissue, and
   associating a particular upper bound with the particular point, the particular upper bound substantially greater than the prescription dose.

20. The method of claim 19, wherein:
   a third tissue type of the plurality of tissue types is associated with slowly-proliferating cells of a different gland; and
   the step of associating at least one of the upper bound and the lower bound further comprises
      determining whether the third tissue type is associated with a particular point in the tissue grid; and
      if it is determined that the third tissue type is associated with the particular point, then associating a different upper bound with the particular point, the different upper bound substantially greater than the prescription dose but substantially less than the particular upper bound associated with the first tissue type.

21. The method of claim 16, wherein:
   a third tissue type of the plurality of tissue types is associated with non-tumor cells; and
   the step of associating at least one of the upper bound and the lower bound further comprises
      determining whether the third tissue type is associated with a particular point in the tissue grid; and
      if it is determined that the third tissue type is associate with the particular point, then associating a particular upper bound with the particular point, the particular upper bound substantially equal to a prescription dose allowed for healthy tissue.

22. The method of claim 16, wherein:
   a third tissue type of the plurality of tissue types is associated with non-tumor cells; and
   the step of associating at least one of the upper bound and the lower bound further comprises
      determining whether the third tissue type is associated with a particular point in the tissue grid; and
      if it is determined that the third tissue type is associate with the particular point, then associating no lower bound with the particular point.

23. The method of claim 16, wherein:
   a third tissue type of the plurality of tissue types is associated with slowly proliferating tumor cells of a different gland; and
   the step of associating at least one of the upper bound and the lower bound further comprises:
      determining whether the third tissue type is associated with a particular point in the tissue grid; and
      if it is determined that the third tissue type is associated with the particular point, then associating a particular upper bound with the particular point, the particular upper bound substantially greater than a prescription dose allowed for healthy tissue.

24. The method of claim 16, wherein:
   a third tissue type of the plurality of tissue types is associated with slowly proliferating tumor cells of a different gland; and
   the step of associating at least one of the upper bound and the lower bound further comprises:
      determining whether the third tissue type is associated with a particular point in the tissue grid; and
      if it is determined that the third tissue type is associated with the particular point, then associating a particular lower bound with the particular point, the particular lower bound substantially equal to a prescription dose allowed for healthy tissue.

25. A method for planning the placement of seeds for a brachytherapy treatment of diseased tissue, the method comprising the steps of:
   representing a placement or non-placement of a seed in each point of a predetermined three dimensional grid of potential seed locations with a binary indicator variable;
   representing a tumor and surrounding tissue as a predetermined three dimensional tissue grid having a plurality of tissue points;
   associating at least one of an upper bound and a lower bound for a dose of radiation received with each point in the tissue grid, wherein a larger upper bound is associated for fast-proliferating tumor cells than for slowly-proliferating tumor cells;
   calculating an objective value based on a difference at each point of the tissue grid between an amount of radiation based on a trial placement of seeds and the at least one of the upper bound and the lower bound;
   varying the trial placement of seeds and repeating the step of calculating the objective value, resulting in additional objective values;
   selecting an optimal objective value from the calculated objective value and the additional objective values; and
   setting a planned placement of seeds based on the trial placement of seeds that obtains the optimal objective value.

26. A method for planning the placement of seeds for a brachytherapy treatment of diseased tissue, the method comprising the steps of:
   representing a placement or non-placement of a seed in each point of a predetermined three dimensional grid of potential seed locations with a binary indicator variable;

representing a tumor and surrounding tissue as a predetermined three dimensional tissue grid having a plurality of tissue points, wherein the tissue grid represents the tumor and surrounding tissue at a particular time, the particular time being an insertion time when the seeds are inserted with needles that cause swelling of the tumor and surrounding tissue;

associating at least one of an upper bound and a lower bound for a dose of radiation received with each point in the tissue grid;

calculating an objective value based on a difference at each point of the tissue grid between an amount of radiation based on a trial placement of seeds and the at least one of the upper bound and the lower bound;

varying the trial placement of seeds and repeating the step of calculating the objective value, resulting in additional objective values;

selecting an optimal objective value from the calculated objective value and the additional objective values; and setting a planned placement of seeds based on the trial placement of seeds that obtains the optimal objective value.

27. A method for planning the placement of seeds for a brachytherapy treatment of diseased tissue, the method comprising the steps of:

representing a placement or non-placement of a seed in each point of a predetermined three dimensional grid of potential seed locations with a binary indicator variable;

representing a tumor and surrounding tissue as a predetermined three dimensional tissue grid having a plurality of tissue points, wherein the tissue grid represents the tumor and surrounding tissue at a particular time, the particular time being a post insertion time after the seeds are inserted with needles that cause swelling of the tumor and surrounding tissue, when the swelling has decreased;

associating at least one of an upper bound and a lower bound for a dose of radiation received with each point in the tissue grid;

calculating an objective value based on a difference at each point of the tissue grid between an amount of radiation based on a trial placement of seeds and the at least one of the upper bound and the lower bound;

varying the trial placement of seeds and repeating the step of calculating the objective value, resulting in additional objective values;

selecting an optimal objective value from the calculated objective value and the additional objective values; and setting a planned placement of seeds based on the trial placement of seeds that obtains the optimal objective value.

28. A method for planning the placement of seeds for a brachytherapy treatment of diseased tissue, the method comprising the steps of:

representing a placement or non-placement of a seed in each point of a predetermined three dimensional grid of potential seed locations with a binary indicator variable;

representing a tumor and surrounding tissue as a predetermined three dimensional tissue grid having a plurality of tissue points, wherein the tissue grid represents the tumor and surrounding tissue at a particular time;

associating at least one of an upper bound and a lower bound for a dose of radiation received with each point in the tissue grid;

calculating an objective value based on a difference at each point of the tissue grid between an amount of radiation based on a trial placement of seeds and the at least one of the upper bound and the lower bound;

varying the trial placement of seeds and repeating the step of calculating the objective value, resulting in additional objective values;

selecting an optimal objective value from the calculated objective value and the additional objective values;

setting a planned placement of seeds based on the trial placement of seeds that obtains the optimal objective value; and determining shrinkage of the tumor and surrounding tissue with time based on a half-life decay of an initial increase in volume associated with insertion of needles into the tissue.

29. The method of claim 28, the step of determining the shrinkage further comprising decreasing each linear dimension based on the cube root of the half life decay.

30. A method for planning the placement of seeds for a brachytherapy treatment of diseased tissue, the method comprising the steps of:

representing a placement or non-placement of a seed in each point of a predetermined three dimensional grid of potential seed locations with a binary indicator variable;

representing a tumor and surrounding tissue as a predetermined three dimensional tissue grid having a plurality of tissue points;

associating at least one of an upper bound and a lower bound for a dose of radiation received with each point in the tissue grid, the associating step further comprising the step of estimating the reduction in tumor parameters corresponding to associating a different upper bound for fast-proliferating tumor cells than for slowly-proliferating tumor cells;

calculating an objective value based on a difference at each point of the tissue grid between an amount of radiation based on a trial placement of seeds and the at least one of the upper bound and the lower bound;

varying the trial placement of seeds and repeating the step of calculating the objective value, resulting in additional objective values;

selecting an optimal objective value from the calculated objective value and the additional objective values; and setting a planned placement of seeds based on the trial placement of seeds that obtains the optimal objective value.

31. A computer system for planning the placement of seeds for a brachytherapy treatment of diseased tissue, the computer system comprising:

a computer readable medium; and one or more processors connected to the computer readable medium, the one or more processors configured to perform the steps of:

representing a placement or non-placement of a seed in each point of a predetermined three dimensional grid of potential seed locations with a binary indicator variable;

representing a tumor and surrounding tissue as a predetermined three dimensional tissue grid having a plurality of tissue points;

associating at least one of an upper bound and a lower bound for a dose of radiation received with each point in the tissue grid;

calculating an objective value based on a difference at each point of the tissue grid between an amount of radiation based on a trial placement of seeds an the at least one of the upper bound and the lower bound;

varying the trial placement of seeds and repeating the step of calculating an objective value resulting in additional objective values;

selecting an optimal objective value from the calculated objective value and the additional objective values; and setting a planned placement of seeds based on the trial placement of seeds that obtains the optimal objective value.

32. The computer system of claim 31, the step of representing a tumor and surrounding tissue based on biological imaging.

33. The computer system of claim 31, wherein the tissue grid represents the tumor and surrounding tissue at a particular time.

34. The computer system of claim 33, further comprising mapping the three dimensional grid of potential seed locations at a time of seed insertion to a new grid of potential seed locations at the particular time.

35. A computer system for planning the placement of seeds for a brachytherapy treatment of diseased tissue, the computer system comprising:

a computer readable medium; and one or more processors connected to the computer readable medium, the one or more processors configured to perform the steps of:

representing a placement or non-placement of a seed in each point of a predetermined three dimensional grid of potential seed locations with a binary indicator variable;

representing a tumor and surrounding tissue as a predetermined three dimensional tissue grid having a plurality of tissue points;

associating at least one of an upper bound and a lower bound for a dose of radiation received with each point in the tissue grid, wherein the step of associating at least one of the upper bound and the lower bound further comprises associating a larger upper bound for fast-proliferating tumor cells than for slowly-proliferating tumor cells;

calculating an objective value based on a difference at each point of the tissue grid between an amount of radiation based on a trial placement of seeds an the at least one of the upper bound and the lower bound;

varying the trial placement of seeds and repeating the step of calculating an objective value resulting in additional objective values;

selecting an optimal objective value from the calculated objective value and the additional objective values; and setting a planned placement of seeds based on the trial placement of seeds that obtains the optimal objective value.

36. A computer readable medium having stored thereon sequences of instructions for planning the placement of seeds for a brachytherapy treatment of diseased tissue, the sequences of instructions causing one or more processors to perform the steps of:

representing a placement or non-placement of a seed in each point of a predetermined three dimensional grid of potential seed locations with a binary indicator variable;

representing a tumor and surrounding tissue as a predetermined three dimensional tissue grid having a plurality of tissue points;

associating at least one of an upper bound and a lower bound for a dose of radiation received with each point in the tissue grid;

calculating an objective value based on a difference at each point of the tissue grid between an amount of radiation based on a trial placement of seeds an the at least one of the upper bound and the lower bound;

varying the trial placement of seeds to obtain an optimal value and repeating the step of calculating an objective value resulting in additional objective values; and setting a planned placement of seeds based on the trial placement of seeds that obtains the optimal objective value.

37. The computer readable medium of claim 36, the step of representing a tumor and surrounding tissue based on biological imaging.

38. The computer readable medium of claim 36, wherein the tissue grid represents the tumor and surrounding tissue at a particular time.

39. The computer readable medium of claim 38, further causing the one or more processors to perform the step of mapping the three dimensional grid of potential seed locations at a time of seed insertion to a new grid of potential seed locations at the particular time.

40. A computer readable medium having stored thereon sequences of instructions for planning the placement of seeds for a brachytherapy treatment of diseased tissue, the sequences of instructions causing one or more processors to perform the steps of:

representing a placement or non-placement of a seed in each point of a predetermined three dimensional grid of potential seed locations with a binary indicator variable;

representing a tumor and surrounding tissue as a predetermined three dimensional tissue grid having a plurality of tissue points;

associating at least one of an upper bound and a lower bound for a dose of radiation received with each point in the tissue grid, wherein the step of associating at least one of the upper bound and the lower bound further comprising associating a larger upper bound for fast-proliferating tumor cells than for slowly-proliferating tumor cells;

calculating an objective value based on a difference at each point of the tissue grid between an amount of radiation based on a trial placement of seeds an the at least one of the upper bound and the lower bound;

varying the trial placement of seeds to obtain an optimal value and repeating the step of calculating an objective value resulting in additional objective values; and setting a planned placement of seeds based on the trial placement of seeds that obtains the optimal objective value.

* * * * *

UNITED STATES PATENT AND TRADEMARK OFFICE
CERTIFICATE OF CORRECTION

PATENT NO. : 6,530,873 B1
DATED : March 11, 2003
INVENTOR(S) : Eva K. Lee

It is certified that error appears in the above-identified patent and that said Letters Patent is hereby corrected as shown below:

Column 3,
Line 10, delete "1a and 1n" and replace with -- 1a – 1n --.

Column 17,
Lines 9 and 11-12, delete "1a and 1n" and replace with -- 1a – 1n --.
Line 16, delete "1a – 1n" and replace with -- 1a – 1g --.

Column 35,
Lines 5-7, delete "varying the trial placement of seeds and repeating the step of calculating an objective value resulting in additional objective values" and replace with -- varying the trial placement of seeds to obtain an optimal value for the objective value --.

Signed and Sealed this

Twelfth Day of August, 2003

JAMES E. ROGAN
*Director of the United States Patent and Trademark Office*